(12) United States Patent
Wright et al.

(10) Patent No.: US 7,871,782 B2
(45) Date of Patent: Jan. 18, 2011

(54) SPECIFIC BINDING MEMBERS AGAINST SYNAPTOPHYSIN

(75) Inventors: Matthew Wright, Aberdeen (GB); Andy Porter, Aberdeen (GB)

(73) Assignee: The University Court of the University of Aberdeen, Aberdeen, Aberdeenshire (GB)

( * ) Notice: Subject to any disclaimer, the term of this patent is extended or adjusted under 35 U.S.C. 154(b) by 953 days.

(21) Appl. No.: 11/547,368

(22) PCT Filed: Mar. 29, 2005

(86) PCT No.: PCT/GB2005/001190
§ 371 (c)(1), (2), (4) Date: Oct. 20, 2006

(87) PCT Pub. No.: WO2005/095453
PCT Pub. Date: Oct. 13, 2005

(65) Prior Publication Data
US 2008/0274123 A1 Nov. 6, 2008

(30) Foreign Application Priority Data
Mar. 29, 2004 (GB) ................................ 0407059.5
Jul. 22, 2004 (GB) ................................ 0416402.6

(51) Int. Cl.
*A61K 39/00* (2006.01)
*G01N 33/53* (2006.01)
(52) U.S. Cl. .................. 435/7.1; 530/387.1; 530/389.2
(58) Field of Classification Search ........................ None
See application file for complete search history.

(56) References Cited

U.S. PATENT DOCUMENTS

| | | | |
|---|---|---|---|
| 5,346,813 A | 9/1994 | Bodenmueller et al. | |
| 5,496,705 A | 3/1996 | Sugano et al. | |
| 5,859,205 A * | 1/1999 | Adair et al. ............... | 530/387.3 |

FOREIGN PATENT DOCUMENTS

WO 99/20749 4/1999

OTHER PUBLICATIONS

Klimka et al., Human anti-CD30 recombinant antibodies by guided phage antibody selection using cell panning. British Journal of Cancer (2000) 83:252-260.*
Beiboer et al.,Guided selection of a pan carcinoma specific antibody reveals similar binding characteristics yet structural divergence between the original murine antibody and its human equivalent. J. Mol., Biol. (2000) 296:833-849.*
Eduardo Padlan, Anatomy of the antibody molecule. Mol Immunol. Feb. 1994;31(3):169-217.*
Portolano et al.,Lack of promiscuity in autoantigen-specific H and L chain combinations as revealed by human H and L chain "roulette". J Immunol. Feb. 1, 1993;150(3):880-7.*
Paul, Fundamental Immunology, 3rd Edition, 1993, pp. 292-295.*
Rudikoff et al Single amino acid substitution altering antigen-binding specificity. Proc Natl Acad Sci U S A. Mar. 1982;79(6): 1979-83.*
MacCallum et al Antibody-antigen interactions: contact analysis and binding site topography. J Mol Biol. Oct. 11, 1996;262(5):732-45.*
Casset et al. A peptide mimetic of an anti-CD4 monoclonal antibody by rational desig. Biochem Biophys Res Commun. Jul. 18, 2003;307(1 ): 198-205.*
Douglass et al., Antibody-targeted myofibroblast apoptosis reduces fibrosis during sustained liver injury. The Journal of Hepatology, 2008, 49:88-98.*
Vajdos FF, et al., "Comprehensive functional maps of the antigen-binding site of an anti-ErbB2 antibody obtained with shotgun scanning mutagenesis," J Mol Biol. Jul. 5, 2002;320(2):415-28.*
International Search Report and Written Opinion for Application No. PCT/GB2005/001190 dated Feb. 27, 2006 (13 pages).
Beljaars, L. et al., "Albumin modified with mannose 6-phosphate: a potential carrier for selective delivery of antifibrotic drugs to rat and human hepatic stellate cells," Hepatology (1999) 29:1486-1493.
Beljaars, L. et al., "Successful targeting to rat hepatic stellate cells using albumin modified with cyclic peptides that recognize the collagen type VI receptor," J. Biol. Chem. (2000) 275(17):12743-12751.
Cassiman, D. et al., "Hepatic stellate cell/myofibroblast subpopulations in fibrotic human and rat livers," J. Hepatology (2002) 36(2):200-209.
Elrick, L.J. et al., "Generation of monoclonal human single chain antibody fragment to hepatic stellate cells—a potential mechanism for targeting liver anti-fibrotic therapeutics," J. Hepatology (2005) 42(6):888-896.

* cited by examiner

*Primary Examiner*—Maher M Haddad
(74) *Attorney, Agent, or Firm*—Michael Best & Friedrich LLP

(57) ABSTRACT

The present invention provides specific binding members that bind synaptophysin and which comprise: an antibody VH domain selected from the group consisting of the C1-3 VH domain (SEQ ID NO. 2) and a VH domain comprising a VH CDR3 with the amino acid sequence of SEQ ID NO. 12 and optionally one or more VH CDR's with an amino acid sequence selected from SEQ ID NO. 10 and SEQ ID NO. 11; and/or an antibody VL domain selected front the group consisting of the C1-3 VL domain (SEQ ID NO. 4) and a VL domain comprising one or more VL CDR's with an amino acid sequence selected from SEQ ID NO. 13, SEQ ID NO. 14 and SEQ ID NO. 15. The invention further provides related materials such as nucleic acids, kits and compositions, and also methods of use of the binding member, for instance in targeting entities to hepatic stellate cells which are implicated it liver fibrosis.

17 Claims, 15 Drawing Sheets

Figure 4

```
        NcoI
    CC ATG GCC GAA GTG CAG CTG TTG GAG TCT GGG GGA GGC TTG GTA
1      Met Ala Glu Val Gln Leu Leu Glu Ser Gly Gly Gly Leu Val

CAG CCT GGG GGG TCC CTG AGA CTC TCC TGT GCA GCC TCT GGA
15     Gln Pro Gly Gly Ser Leu Arg Leu Ser Cys Ala Ala Ser Gly
                       HCDR 1                    HFW2
       TTC ACC TTT AGC AGC TAT GCC ATG AGC TGG GTC CGC CAG GCT
30     Phe Thr Phe Ser Ser Tyr Ala Met Ser Trp Val Arg Gln Ala
                                                CDR 2
       CCA GGG AAG GGG CTG GAG TGG GTC TCA ACT ATT GCT GCG TCG
45     Pro Gly Lys Gly Leu Glu Trp Val Ser Thr Ile Ala Ala Ser
                       HCDR 2                         HFW3
       GGT CCT TCT ACA GGG TAC GCA GAC TCC GTG AAG GGC CGG TTC
60     Gly Pro Ser Thr Gly Tyr Ala Asp Ser Val Lys Gly Arg Phe

ACC ATC TCC AGA GAC AAT TCC AAG AAC ACG CTG TAT CTG CAA
75     Thr Ile Ser Arg Asp Asn Ser Lys Asn Thr Leu Tyr Leu Gln

ATG AAC AGC CTG AGA GCC GAG GAC ACG GCC GTA TAT TAC TGT
90     Met Asn Ser Leu Arg Ala Glu Asp Thr Ala Val Tyr Tyr Cys
                  HCDR 3                HFW4
       GCG AAA ACT ACG GCG AAG TTT GAC TAC TGG GGC CAG GGA ACC
105    Ala Lys Thr Thr Ala Lys Phe Asp Tyr Trp Gly Gln Gly Thr
                                              Linker
       CTG GTC ACC GTC TCG AGC GGT GGA GGC GGT TCA GGC GGA GGT
120    Leu Val Thr Val Ser Ser Gly Gly Gly Gly Ser Gly Gly Gly
            Linker          LFW1
       GGC AGC GGC GGT GGC GGG TCG ACG GAC ATC CAG ATG ACC CAG
135    Gly Ser Gly Gly Gly Gly Ser Thr Asp Ile Gln Met Thr Gln TCT CCA TCC TCC CTG TCT GCA TCT GTA GGA GAC AGA GTC ACC
150    Ser Pro Ser Ser Leu Ser Ala Ser Val Gly Asp Arg Val Thr
                                  LCDR 1
       ATC ACT TGC CGG GCA AGT CAG AGC ATT AGC AGC TAT TTA AAT
165    Ile Thr Cys Arg Ala Ser Gln Ser Ile Ser Ser Tyr Leu Asn
         LFW2
       TGG TAT CAG CAG AAA CCA GGG AAA GCC CCT AAG CTC CTG ATC
180    Trp Tyr Gln Gln Lys Pro Gly Lys Ala Pro Lys Leu Leu Ile
                   LCDR2                       LFW3
       TAT TCT GCA TCC CGA TTG CAA AGT GGG GTC CCA TCA AGG TTC
195    Tyr Ser Ala Ser Arg Leu Gln Ser Gly Val Pro Ser Arg Phe
```

Figure 4 Continued

```
         AAT GGC AGT GGA TCT GGG ACA GAT TTC ACT CTC ACC ATC AGC
     210 Asn Gly Ser Gly Ser Gly Thr Asp Phe Thr Leu Thr Ile Ser

LCDR3
         AGT CTG CAA CCT GAA GAT TTT GCA ACT TAC TAC TGT CAA CAG
     225 Ser Leu Gln Pro Glu Asp Phe Ala Thr Tyr Tyr Cys Gln Gln

LCDR3                                 LFW4
         CTG CAG AGG AAG CCT ACG ACG TTC GGC CAA GGG ACC AAG GTG GAA
     240 Leu Gln Arg Lys Pro Thr Thr Phe Gly Gln Gly Thr Lys Val Glu

NotI       Beginning CK domain
         ATC AAA CGG GCG GCC GCT GCA CCA TCT GTC TTC ATC TTT
     255 Ile Lys Arg Gly Ala Ala Ala Pro Ser Val Phe Ile Phe
```

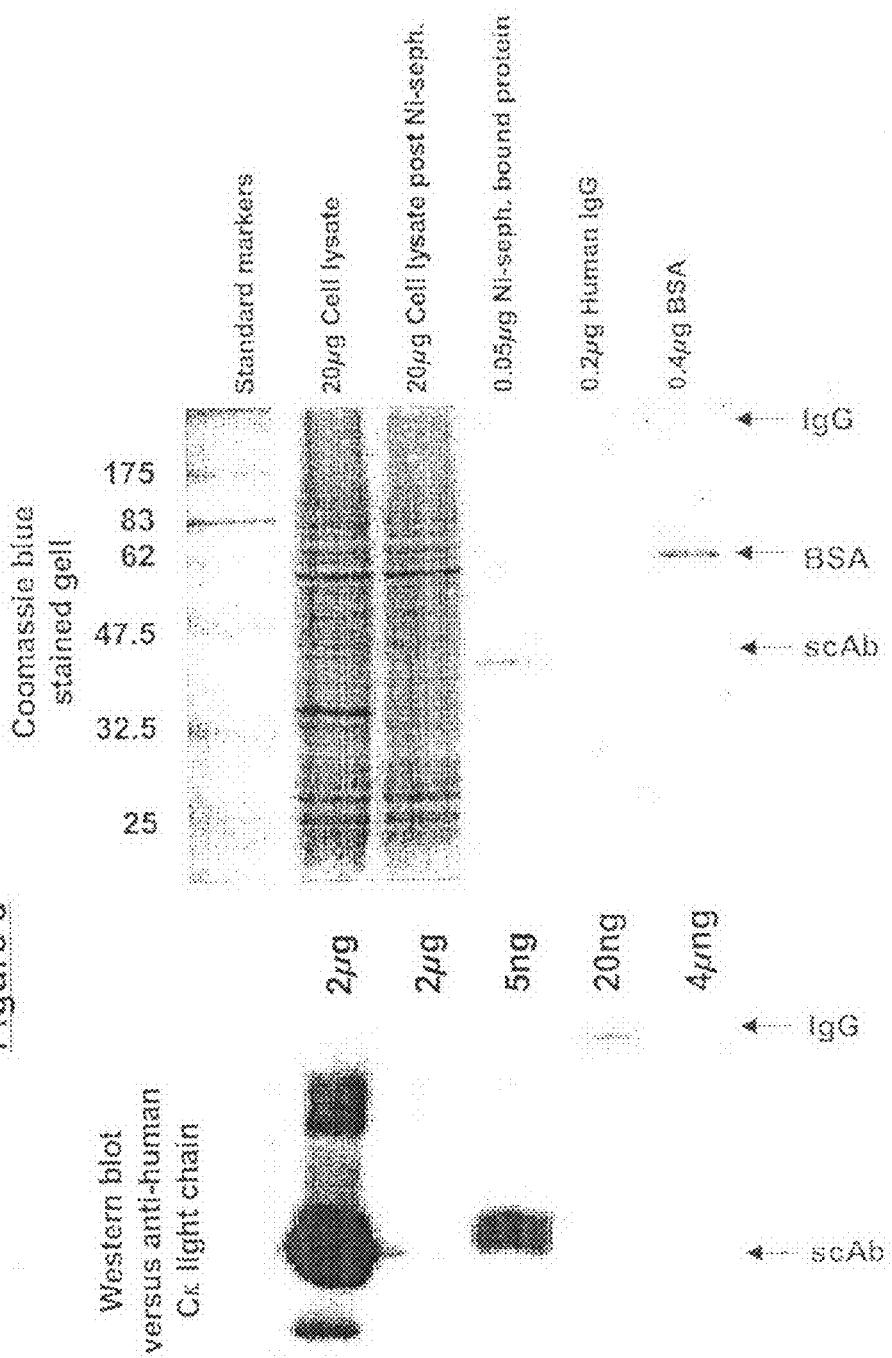

SPECIFIC BINDING MEMBERS AGAINST SYNAPTOPHYSIN

CROSS-REFERENCE TO RELATED APPLICATIONS

This patent application is a national stage filing under 35 U.S.C. 371 of International Application No. PCT/GB2005/001190 filed on Mar. 29, 2005, which claims foreign priority benefits to United Kingdom Application Nos. 0407059.5 filed on Mar. 29, 2004 and 0416402.6 filed on Jul. 22, 2004.

The present invention relates to specific binding members directed to synaptophysin. Preferred embodiments of the present invention employ the antibody VH and/or VL domain of the scFv fragment herein termed C1-3. Further preferred embodiments employ one or more complementarity determining regions (CDRs) of the C1-3 heavy chain variable (VH) and/or light chain variable (VL) domains, especially VH C1-3 in other antibody framework regions. The inventors have identified a number of antibody molecules with advantageous properties, especially the ability to target to the outer surface of hepatic stellate cells.

Liver fibrosis is a reversible process characterised by an accumulation of extracellular matrix protein in the liver that precedes the development of cirrhosis and liver failure (Friedman S. L. J Biol Chem 2000; 275:2247-50; Bataller R. et al. Semin Liver Dis 2001; 21:437-51). A number of conditions can cause damage to the liver resulting in fibrosis, including viral infections (e.g. Hepatitis C) and alcohol misuse. Fibrosis can remain undetected for many years and can inflict severe damage that is sometimes fatal. Despite a global population of in excess of potentially 200 million people suffering from liver fibrosis, there are no therapeutic options available to clinicians to treat this condition.

Liver fibrosis is caused by hepatic stellate cells (HSC) in response to chronic liver damage. HSCs play the primary and central role in the development and resolution of liver fibrosis. HSCs exist in normal liver in a quiescent state and function to store vitamin A (Geerts A. Semin Liver Dis 2001; 21:311-35). In response to chronic liver damage, the quiescent HSCs "activate" to a myofibroblast-like phenotype. The activated HSCs proliferate and are believed to express the majority of extracellular matrix proteins that constitute the scarring observed in liver fibrosis. There is strong evidence to suggest that activated HSCs and fibrogenesis are deleterious responses to chronic liver damage of any cause and that increased activated HSC apoptosis can resolve fibrosis and enhance the liver's response to chronic damage (Iredale J. P. et al. J Clin Invest 1998; 102:538-49; Wright M. C. et al. Gastroenterology 2001; 121:685-98; Orr J. G. et al. Hepatology 2004; 40:232-42; Issa R. et al. Gut 2001; 48:548-57).

A major problem for many potential anti-fibrotics in the past is that the drugs did not reach therapeutic concentrations within hepatic stellate cells, possibly because of the proximity of hepatocytes, which function to metabolise exogenous compounds. These drugs include a number of agents that have anti-inflammatory activity in vitro and in vivo and which may reduce stellate cell activation. These include corticosteroids, antagonists to TNFα, anti-oxidants, cytokines (γ interferon) and hepatocytes growth factor (HGF) PPARγ ligands (thiazolidinediones), endothelin-1 antagonists, halofuginone (an anticoccidial drug) and gene therapy (administration of metalloproteinase mRNA via gene therapy in animal models). The lack of success indicates that it would be useful to target any anti-fibrotic therapies to hepatic stellate cells in the liver.

It has been shown recently by Polestra and colleagues that the mannose 6-phosphate/insulin-like growth factor II (M6P/IGF-II) receptor is expressed at high levels in activated hepatic stellate cells during fibrosis and that serum albumin (SA) modified with mannose 6-phosphate (M6P) distributes to the liver when administered to rats (molar ratio of M6P:SA is 28:1) with 70% of the intra hepatic dose found in hepatic stellate cells (Beljaars et al. Hepatology 1999; 29: 1486-93). SA modified with 10 cyclic peptide moieties recognizing collagen type VI receptors also results in preferential distribution to the rat liver within 10 minutes after intravenous injection (Beljaars et al. J Biol Chem 2000; 275: 12743-51). In fibrotic livers 70% of the hepatic dose of the peptide-modified albumin was associated with activated hepatic stellate cells. However, in human liver tissue perfusions, these reagents were taken up by kupffer cells, the hepatic cell type involved in the removal of large molecular weight molecules and foreign particles, and not stellate cells.

Synaptophysin is a protein expressed in neural cells and hepatic stellate cells only (Cassiman D. et al. Am J Pathol 1999; 155:1831-1839; Bargou R. C. et al. Gene 1991; 99:197-204). It is a membrane bound protein and is not available in a functional purified form. Despite this significant limitation the applicants have isolated successfully the first fully human monoclonal antibody fragment with specificity for an extracellular domain of synaptophysin, present on hepatic stellate cells. This antibody was isolated using the technique of phage display and a human antibody library made available by the MRC, Cambridge, UK. The antibody was raised against a peptide and it is this anti-peptide antibody that also recognises the whole native synaptophysin protein in its natural confirmation in the stellate cell membrane. Antibodies which recognise and bind to synaptophysin have the potential to provide, for the first time, a reagent suitable for a number of therapeutic applications as discussed below.

Schematic diagram of synaptophysin. Human synaptophysin has a theoretical molecular mass of 33.8 kDa and is predicted to span the plasma membrane of cells as outlined. The protein is reported to be glycosylated and experimentally has a molecular mass of ~38-40 kDa (Eastwood S. L. et al. Brain Res Bull 2001; 55:569-78).

FIG. 2

Isolation and amplification of phage-antibodies (polyclonal) with affinity for the target peptide-BSA. The enrichment of phage-antibodies (polyclonal) recognising the target peptide-BSA antigen during bio-panning was assessed by ELISA. Polyclonal phage-antibodies (~1×10$^{10}$) rescued from each round of selection were assayed for binding to the target peptide-BSA conjugate. Bound phage were detected using HRP-labelled anti-M13 antibody (Pharmacia) as outlined in methods section. Phage titre at each pan is indicated ( - - - ☐- - - ).

FIG. 3

Figure 2:
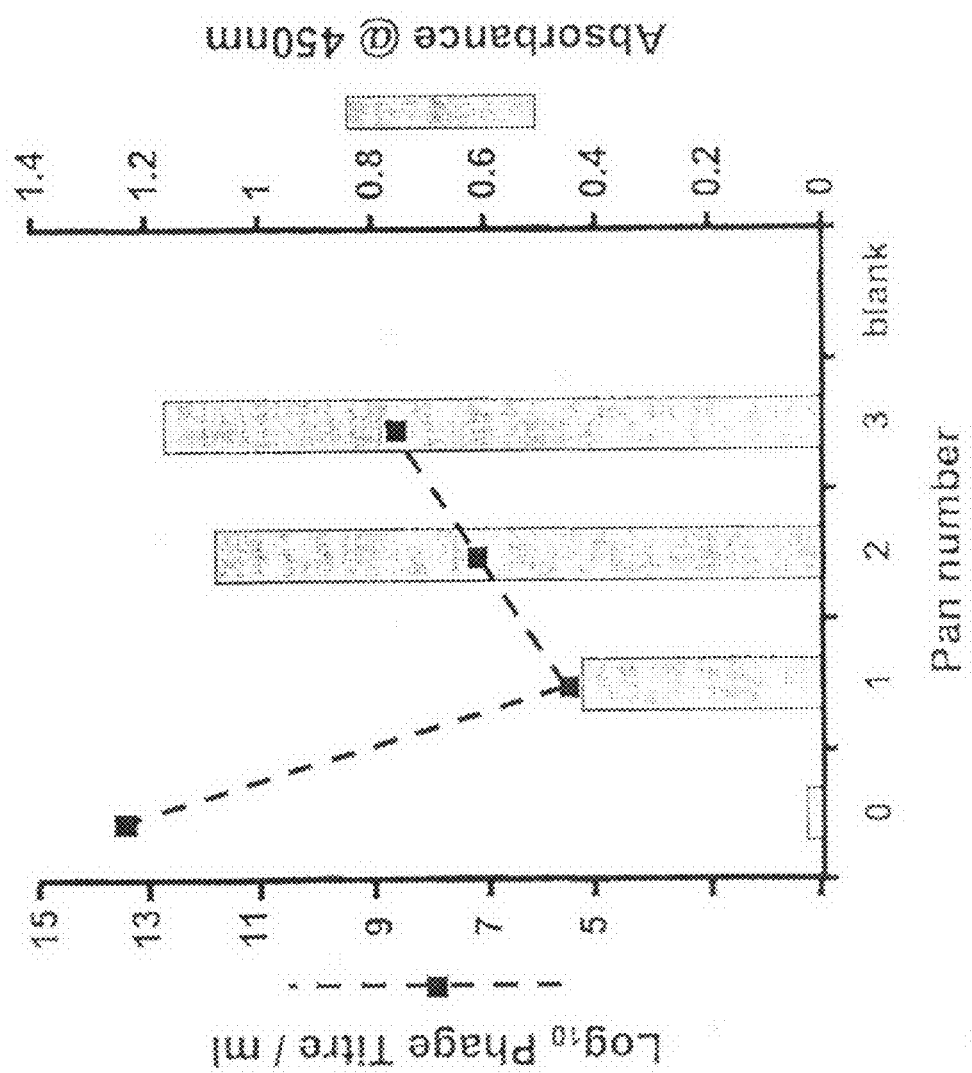

C1-phage antibody clone (monoclonal) assayed for binding to the target peptide-BSA as outlined for FIG. 2.

FIG. 4

Nucleotide and amino acid sequence of the C1-3 scAb within the pIMS147 vector (alignment of SEQ ID NO 7 and SEQ ID NO 8). The hypervariable complementarity determining regions (CDRs), which make up the antigen binding site, are in bold. The flexible amino acid linker (Gly$_4$Ser)$_3$ that joins the H and L chains is underline (_____). The start of the Framework regions (FW) and the start of the Human constant kappa domain (C$_K$) are also indicated. Cloning sites are underlined (_____) with the corresponding restriction enzyme indicated above the amino acid sequence. The beginning of the HuCk constant domain and 6 Histidine residue purification tag is shown—full amino acid sequence:

(SEQ ID NO 16)
AAPSVFIFPPSDEQLKSGTASVVCLLNNFYPREAKVQWKVDNALQSGNSQ

ESVTEQDSKDSTYSLSSTLTLSKADYEKHKVYACEVTHQGLSSPVTKSFN

RGESHHHHHH

FIG. 5

Induction of C1-3 scAb expression in XL-1 blue cells and purification by Ni affinity chromatography. Upper blot, coomassie blue stained samples after SDS-PAGE with protein loadings as indicated; lower blot, Western analysis of samples with anti-human Cκ light chain antibody.

FIG. 6

Anti-human Cκ light chain capture ELISA quantitation of C1-3 scAb. Goat anti-human Cκ light chain antibody was coated onto the surface of a ninety six well plate. Dilutions of human IgG or C1-3 scAb preparation were incubated in individual wells. After extensive washing, captured IgG (-□-) or scAb (-o-) was quantitated as outlined in the methods section. Data are the mean and standard deviation of 3 separate determinations—typical of 7 separate preparations.

FIG. 7

Expressed scAb was tested for its ability to interact with the peptide YPFRLHQVYFDAPSC (SEQ ID NO: 9) by ELISA using anti-BSA-target peptide scAb. Wells of a 96 well plate were coated with BSA-target peptide or BSA and incubated with either C1-3 scAb (grey bars) or control scAb incubation buffer (clear bars) followed by extensive washing. Bound scAb was detected using the HRP conjugated anti-human Cκ light chain antibody and quantitated as outlined in methods section. Data are the mean and standard deviation of 3 separate determinations. 'BSA-peptide 2' is the target peptide.

FIG. 8

Western blot showing the binding of C1-3 scAb to the target peptide. Cell extracts (5 μg/lane) were subjected to Western blotting and membranes probed with C1-3 scAb followed by incubation with HRP conjugated anti-human Cκ light chain antibody and detection using ECL reagent. rHSCs—rat hepatic stellate cells; hHSCs—human hepatic stellate cells (AH4=anonymous patient code); rHCs—rat hepatocytes; B13—rat pancreatic stem cell; B13-H—rat pancreatic stem cell after trans-differentiation into an hepatocyte.

FIG. 9

C1-3 scFv was labelled with FITC and confirmed by SDS-PAGE. $Ni^{2+}$ charged IMAC Fast Flow Sepharose resin purified C1-3 acAb was subjected to dialysis and then concentrated using a centricon YM-3 centrifugal concentrator. Concentrated C1-3 scAb was then FITC-labelled and aliquots of each fraction (approx 0.1 μg/lane) subjected to SDS-PAGE followed by coomassie blue (total protein) staining of gel.

FIG. 10

FACS analysis of human HSC incubated without (UPPER PANEL) or with (LOWER PANEL) primary antibodies—i.e. FITC-C13 scAb (FITC) and a mouse monoclonal antibody to α-smooth muscle actin (αsma-APC). Anti-α-smooth muscle actin antibody was detected using a biotin conjugated secondary antibody followed by fluorophore-streptavidin conjugate incubation as outlined in the Methods section. Figures represent the percentage of cells in each quadrant. Data are typical of 3 separate cell preparations.

FIG. 11

Uptake of C1-3 scAb and C1-3-conjugates by human HSCs in culture. HSCs seeded into 24 well plates were incubated in 0.3 mls culture medium containing 5 μg scAb. Samples of medium were taken at the indicated times and subjected to Western blotting to detect scAb using HRP-conjugated anti-human Cκ light chain antibody (UPPER PANEL) and serum albumin (LOWER PANEL) as a loading control. Results typical of 4 separate experiments.

FIG. 12

Effect of scAb incubation on HSC viability. HSCs seeded into 24 well plates were incubated in 0.3 mls culture medium containing 5 μg scAb or the indicated-chemical. Cells were incubated for 3 hours prior to removal of medium and washing with 1×PBS. Attachment (as a measure of viability) was determined by a direct protein assay in the culture wells. Data are the mean and standard deviation of 3 separate wells from the same experiment, typical of 3 separate experiments. *Significantly different from control using Student T test (two tailed) $P>95\%$.

FIG. 13

Effect of synaptophysin peptides and monensin on FITC-C1-3 scAb binding to human HSCs. Human HSCs seeded into 24 well plates were washed and incubated in 500 μl Hepes/HBSS per well for 1 hour containing either: 10 μg C1-3 scAb; 10 μg FITC-C1-3 scAb; 10 μg FITC-C1-3 scAb and 0.25 nmoles of the target peptide; 10 μg FITC-C1-3 scAb and 2.5 nmoles of the target peptide; 10 μg FITC-C1-3 scAb and 25 nmoles of the target peptide; 10 μg FITC-C1-3 scAb and 25 nmoles of the target peptide P1; 10 μg FITC-C1-3 scAb and 2.5 μM monensin; 10 μg FITC-C1-3 scAb and 15 μM monensin; 10 μg FITC-3A8 scAb (scAb raised to microcystin and not expected to bind to HSCs). Cells incubated with monensin were preincubated for 10 minutes. Just prior to addition of scAb, the medium was changed and cells were re-dosed with monensin. The figure shows quantitative analysis of mean percentage fluorescent cells/field of view±standard deviation, from 20 randomly selected fields. Bar=μm. Monen=monensin; P1=the ATDPENIIKEMPMC peptide (SEQ ID NO 27); P2=the target peptide.

FIG. 14

HSC viability. Human HSCs in 24 well plate culture were treated with 500 ul medium containing either DMSO vehicle; 1.5 uM gliotoxin (750 pmoles); 20 ul C1-3 scAb at 1 mg/ml (20 ug C1-3 scAb); or 20 ul C1-3-gliotoxin conjugate at 0.5 mg/ml (10 ug C1-3 scAb-250 pmoles C1-3 scAb*/1000 pmoles gliotoxidn).

*0.5 mg C1-3 protein/ml stock=12.5 uM=12.5 nmoles/ml=12.5 pmol/ul

The following sequences are disclosed herein:
SEQ ID NO: 1 C1-3 VH encoding nucleotide sequence
SEQ ID NO: 2 C1-3 VH amino acid sequence
SEQ ID NO: 3 C1-3 VL encoding nucleotide sequence
SEQ ID NO: 4 C1-3 VL amino acid sequence
SEQ ID NO: 5 C1-3 linker encoding nucleotide sequence
SEQ ID NO: 6 C1-3 linker amino acid sequence
SEQ ID NO: 7 C1-3 encoding nucleotide sequence
SEQ ID NO: 8 C1-3 amino acid sequence
SEQ ID NO: 9 C1-3 antigen
SEQ ID NO: 10 C1-3 VH CDR1, within VH amino acid sequence (SEQ ID NO: 2).
SEQ ID NO: 11 C1-3 VH CDR2, within VH amino acid sequence (SEQ ID NO: 2).
SEQ ID NO: 12 C1-3 VH CDR3, within VH amino acid sequence (SEQ ID NO: 2).
SEQ ID NO: 13 C1-3 VL CDR1, within VL amino acid sequence (SEQ ID NO: 4).

SEQ ID NO: 14 C1-3 VL CDR2, within VL amino acid sequence (SEQ ID NO: 4).

SEQ ID NO: 15 C1-3 VL CDR3, within VL amino acid sequence (SEQ ID NO: 4).

SEQ ID NO: 16 Entire amino acid sequence (single letter code) for the Human constant kappa domain (Hu $C_K$) and 6 Histidine residue purification tag—light chain Framework 4 (LFW4) ends and Hu $C_K$ begins at the end of NotI site.

SEQ ID NO: 17 an earlier version of the C1-3 VL, encoding nucleotide sequence.

SEQ ID NO: 18 an earlier version of the C1-3 VL amino acid sequence.

SEQ ID NO: 19 an earlier version of the C1-3 encoding nucleotide sequence.

SEQ ID NO: 20 an earlier version of the C1-3 amino acid sequence.

In the above sequences, as in FIG. 4, the hypervariable complementarity determining regions (CDRs), which make up the antigen binding site, are in bold. The flexible amino acid linker ($Gly_4$, $Ser)_3$ that joins the H and L chains is underlined (_____). The start of the Framework regions (FW) and the start of the Human constant kappa domain ($C_K$) are also indicated. Cloning sites are underlined (_____) with the corresponding restriction enzyme indicated above the amino acid sequence.

In one aspect, the present invention provides a specific binding member which binds synaptophysin and which comprises the C1-3 VH domain (SEQ ID NO: 2) and/or the C1-3 VL domain (SEQ ID NO: 4).

Generally, a VH domain is paired with a VL domain to provide an antibody antigen binding site, although as discussed further below a VH domain alone may be used to bind antigen. In one preferred embodiment, the C1-3 VH domain (SEQ ID NO: 2) is paired with the C1-3 VL domain (SEQ ID NO: 4), so that an antibody antigen binding site is formed comprising both the C1-3 VH and VL domains. In other embodiments, the C1-3 VH is paired with a VL domain other than the C1-3 VL. Light-chain promiscuity is well established in the art.

One or more CDR's may be taken from the C1-3 VH or VL domain and incorporated into a suitable framework. This is discussed further below. C1-3 VH CDR's 1, 2 and 3 are shown in SEQ ID Nos 10, 11 and 12, respectively. C1-3 VL CDR's 1, 2 and 3 are shown in SEQ ID Nos 13, 14 and 15, respectively.

Variants of the VH and VL domains of which the sequences are set out herein and which can be employed in specific binding members for synaptophysin can be obtained by means of methods of sequence alteration or mutation and screening. Such methods are also provided by the present invention.

Variable domain amino acid sequence variants of any of the VH and VL domains whose sequences are specifically disclosed herein may be employed in accordance with the present invention, as discussed. Particular variants may include one or more amino acid sequence alterations (addition, deletion, substitution and/or insertion of an amino acid residue), maybe less than about 20 alterations, less than about 15 alterations, less than about 10 alterations or less than about 5 alterations, 4, 3, 2 or 1. Alterations may be made in one or more framework regions and/or one or more CDR's.

A specific binding member according to the invention may be one which competes for binding to antigen with any specific binding member which both binds the antigen and comprises a specific binding member, VH and/or VL domain disclosed herein, or VH CDR3 disclosed herein, or variant of any of these. Competition between binding members may be assayed easily in vitro, for example using ELISA and/or by tagging a specific reporter molecule to one binding member which can be detected in the presence of other untagged binding member(s), to enable identification of specific binding members which bind the same epitope or an overlapping epitope.

Thus a further aspect of the present invention provides a specific binding member comprising a human antibody antigen-binding site which competes with C1-3 for binding to synaptophysin.

Various methods are available in the art for obtaining antibodies against synaptophysin and which may compete with C1-3 for binding to synaptophysin.

In a further aspect, the present invention provides a method of obtaining one or more specific binding members able to bind the antigen, the method including bringing into contact a library of specific binding members according to the invention and said antigen, and selecting one or more specific binding members of the library able to bind said antigen.

In a preferred embodiment, the specific binding member binds an epitope within the amino acid sequence YPFRLHQVYFDAPSC (SEQ ID NO: 9).

The library may be displayed on the surface of bacteriophage particles, each particle containing nucleic acid encoding the antibody VH variable domain displayed on its surface, and optionally also a displayed VL domain if present.

Following selection of specific binding members able to bind the antigen and displayed on bacteriophage particles, nucleic acid may be taken from a bacteriophage particle displaying a said selected specific binding member. Such nucleic acid may be used in subsequent production of a specific binding member or an antibody VH variable domain (optionally an antibody VL variable domain) by expression from nucleic acid with the sequence of nucleic acid taken from a bacteriophage particle displaying a said selected specific binding member.

An antibody VH variable domain with the amino acid sequence of an antibody VH variable domain of a said selected specific binding member may be provided in isolated form, as may a specific binding member comprising such a VH domain.

Ability to bind synaptophysin may be further tested, also ability to compete with C1-3 for binding to synaptophysin. Ability to antagonise action of synaptophysin may be tested, as discussed further below.

A specific binding member according to the present invention may bind synaptophysin with the affinity of C1-3. Preferably the specific binding member binds to the epitope YPFRLHQVYFDAPSC of synaptophysin.

The specific binding member may bind to murine, rat and/or human synaptophysin. Preferably the specific binding member binds to human synaptophysin.

Binding affinity and neutralisation potency of different specific binding members can be compared under appropriate conditions.

In addition to antibody sequences, a specific binding member according to the present invention may comprise other amino acids, e.g. forming a peptide or polypeptide, such as a folded domain, or to impart to the molecule another functional characteristic in addition to ability to bind antigen.

Specific binding members of the invention may carry a detectable label, or may be conjugated to a toxin or enzyme (e.g. via a peptidyl bond or linker).

Those skilled in the art are aware of numerous approaches to chemically conjugating molecules to proteins. When the specific binding member is for pharmaceutical use the conjugate bond is preferably stable in circulation but labile once the conjugate is sequestered intracellularly.

In a preferred embodiment of the present invention, the specific binding member can be conjugated to the detectable, fluorescent label Fluorescein isothiocyanate (FITC).

In further aspects, the invention provides an isolated nucleic acid which comprises a sequence encoding a specific binding member, VH domain and/or VL domain according to the present invention, and methods of preparing a specific binding member, a VH domain and/or a VL domain of the invention, which comprise expressing said nucleic acid under conditions to bring about production of said specific binding member, VH domain and/or VL domain, and recovering it.

Specific binding members according to the invention may be used in a method of treatment or diagnosis of the human or animal body, such as a method of treatment (which may include prophylactic treatment) of a disease or disorder in a human patient which comprises administering to said patient an effective amount of a specific binding member of the invention. Conditions treatable in accordance with the present invention include those discussed elsewhere herein.

Specific binding members according to the invention may be used in a method of imaging, for example, to determine the presence or location of cells to which the specific binding member binds.

In a further aspect, the present invention provides a diagnostic kit comprising a specific binding member according to the invention and one or more reagents to determine binding of the specific binding member to the antigen.

A further aspect of the present invention provides nucleic acid, generally isolated, encoding an antibody VH variable domain (SEQ ID NO: 1) and/or VL variable domain (SEQ ID NO: 3) disclosed herein.

Another aspect of the present invention provides nucleic acid, generally isolated, encoding a VH CDR or VL CDR sequence disclosed herein, especially a VH CDR selected from SEQ ID Nos 10, 11 and 12 or a VL CDR selected from SEQ ID Nos 13, 14 and 15, most preferably C1-3 VH CDR3 (SEQ ID NO: 12).

A further aspect provides a host cell transformed with nucleic acid of the invention.

A yet further aspect provides a method of production of an antibody VH variable domain, the method including causing expression from encoding nucleic acid. Such a method may comprise culturing host cells under conditions for production of said antibody VH variable domain.

Analogous methods for production of VL variable domains and specific binding members comprising a VH and/or VL domain are provided as further aspects of the present invention.

A method of production may comprise a step of isolation and/or purification of the product.

A method of production may comprise formulating the product into a composition including at least one additional component, such as a pharmaceutically acceptable excipient.

These and other aspects of the invention are described in further detail below.

TERMINOLOGY

Specific Binding Member

This describes a member of a pair of molecules which have binding specificity for one another. The members of a specific binding pair may be naturally derived or wholly or partially synthetically produced. One member of the pair of molecules has an area on its surface, or a cavity, which specifically binds to and is therefore complementary to a particular spatial and polar organisation of the other member of the pair of molecules. Thus the members of the pair have the property of binding specifically to each other. Examples of types of specific binding pairs are antigen-antibody, biotin-avidin, hormone-hormone receptor, receptor-ligand, enzyme-substrate. This application is concerned with antigen-antibody type reactions.

Antibody Molecule

This describes an immunoglobulin whether natural or partly or wholly synthetically produced. The term also covers any polypeptide or protein comprising an antibody binding domain. Antibody fragments which comprise an antigen binding domain are such as Fab, scFv, Fv, dAb, Fd; and diabodies.

It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP-A-184187, GB 2188638A or EP-A-239400. A hybridoma or other cell producing an antibody may be subject to genetic mutation or other changes, which may or may not alter the binding specificity of antibodies produced.

As antibodies can be modified in a number of ways, the term "antibody molecule" should be construed as covering any specific binding member or substance having an antibody antigen-binding domain with the required specificity. Thus, this term covers antibody fragments and derivatives, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023.

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341, 544-546 (1989)) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988); (viii) bispecific single chain Fv dimers (PCT/US92/09965) and (ix) "diabodies", multivalent or multispecific fragments constructed by gene fusion (WO94/13804; P. Holliger et al, Proc. Natl. Acad. Sci. USA 90, 6444-6448, 1993). Fv, scFv or diabody molecules may be stabilised by the incorporation of disulphide bridges linking the VH and VL domains (Y. Reiter et al, Nature Biotech, 14, 1239-1245, 1996). Minibodies comprising a scFv joined to a CH3 domain may also be made (S. Hu et al, Cancer Res., 56, 3055-3061, 1996).

Where bispecific antibodies are to be used, these may be conventional bispecific antibodies, which can be manufactured in a variety of ways (Holliger, P. and Winter G. Current Opinion Biotechnol. 4, 446-449 (1993)), e.g. prepared chemically or from hybrid hybridomas, or may be any of the bispecific antibody fragments mentioned above. Diabodies and scFv can be constructed without an Fc region, using only variable domains, potentially reducing the effects of anti-idiotypic reaction.

Bispecific diabodies, as opposed to bispecific whole antibodies, may also be particularly useful because they can be readily constructed and expressed in *E. coli*. Diabodies (and many other polypeptides such as antibody fragments) of appropriate binding specificities can be readily selected using phage display (WO94/13804) from libraries. If one arm of the diabody is to be kept constant, for instance, with a specificity directed against synaptophysin, then a library can be made where the other arm is varied and an antibody of appropriate specificity selected. Bispecific whole antibodies may be made by knobs-into-holes engineering (J. B. B. Ridgeway et al, Protein Eng., 9, 616-621, 1996).

Antigen Binding Domain

This describes the part of an antibody molecule which comprises the area which specifically binds to and is complementary to part or all of an antigen. Where an antigen is large, an antibody may only bind to a particular part of the antigen, which part is termed an epitope. An antigen binding domain may be provided by one or more antibody variable domains (e.g. a so-called Fd antibody fragment consisting of a VH domain). Preferably, an antigen binding domain comprises an antibody light chain variable region (VL) and an antibody heavy chain variable region (VH).

Specific

This may be used to refer to the situation in which one member of a specific binding pair will not show any significant binding to molecules other than its specific binding partner(s). The term is also applicable where e.g. an antigen binding domain is specific for a particular epitope which is carried by a number of antigens, in which case the specific binding member carrying the antigen binding domain will be able to bind to the various antigens carrying the epitope.

Typically, specificity may be determined by means of a binding assay such as ELISA employing a panel of antigens. A specific binding member according to the present invention may recognise synaptophysin on hepatic stellate cells and not neural cells.

Comprise

This is generally used in the sense of "include", that is to say permitting the presence of one or more features or components.

Isolated

This refers to the state in which specific binding members of the invention, or nucleic acid encoding such binding members, will generally be in accordance with the present invention. Members and nucleic acid will be free or substantially free of material with which they are naturally associated such as other polypeptides or nucleic acids with which they are found in their natural environment, or the environment in which they are prepared (e.g. cell culture) when such preparation is by recombinant DNA technology practised in vitro or in vivo. Members and nucleic acid may be formulated with diluents or adjuvants and still for practical purposes be isolated—for example the members will normally be mixed with gelatin or other carriers if used to coat microtitre plates for use in immunoassays, or will be mixed with pharmaceutically acceptable carriers or diluents when used in diagnosis or therapy. Specific binding members may be glycosylated, either naturally or by systems of heterologous eukaryotic cells (e.g. CHO or NS0 (ECACC 85110503) cells, or they may be (for example if produced by expression in a prokaryotic cell) unglycosylated.

By "substantially as set out" it is meant that the relevant CDR or VH or VL domain of the invention will be either identical or highly similar to the specified regions of which the sequence is set out herein. By "highly similar" it is contemplated that from 1 to 5, preferably from 1 to 4 such as 1 to 3 or 1 or 2, or 3 or 4, amino acid substitutions may be made in the CDR and/or VH or VL domain.

The structure for carrying a CDR of the invention will generally be of an antibody heavy or light chain sequence or substantial portion thereof in which the CDR is located at a location corresponding to the CDR of naturally occurring VH and VL antibody variable domains encoded by rearranged immunoglobulin genes. The structures and locations of immunoglobulin variable domains may be determined by reference to (Kabat, E. A. et al, Sequences of Proteins of Immunological Interest. 4th Edition. US Department of Health and Human Services. 1987, and updates thereof, now available on the Internet (http://immuno.bme.nwu.edu or find "Kabat" using any search engine).

Variable domains employed in the Invention may be obtained from any germ-line or rearranged human variable domain, or may be a synthetic variable domain based on consensus sequences of known human variable domains. A CDR sequence of the invention (e.g. CDR3) may be introduced into a repertoire of variable domains lacking a CDR (e.g. CDR3), using recombinant DNA technology.

For example, Marks et al (*Bio/Technology*, 1992, 10:779-783) describe methods of producing repertoires of antibody variable domains in which consensus primers directed at or adjacent to the 5' end of the variable domain area are used in conjunct-ion with consensus primers to the third framework region of human VH genes to provide a repertoire of VH variable domains lacking a CDR3. Marks et al further describe how this repertoire may be combined with a CDR3 of a particular antibody. Using analogous techniques, the CDR3-derived sequences of the present invention may be shuffled with repertoires of VH or VL domains lacking a CDR3, and the shuffled complete VH or VL domains combined with a cognate VL or VH domain to provide specific binding members of the invention. The repertoire may then be displayed in a suitable host system such as the phage display system of WO92/01047 so that suitable specific binding members may be selected. A repertoire may consist of from anything from $10^4$ individual members upwards, for example from $10^6$ to $10^8$ or $10^{10}$ members.

Analogous shuffling or combinatorial techniques are also disclosed by Stemmer (*Nature*, 1994, 370:389-391), who describes the technique in relation to a β-lactamase gene but observes that the approach may be used for the generation of antibodies.

A further alternative is to generate novel VH or VL regions carrying a CDR-derived sequences of the invention using random mutagenesis of one or more selected VH and/or VL genes to generate mutations within the entire variable domain. Such a technique is described by Gram et al (1992, *Proc. Natl. Acad. Sci., USA*, 89:3576-3580), who used error-prone PCR.

Another method which may be used is to direct mutagenesis to CDR regions of VH or VL genes. Such techniques are disclosed by Barbas et al, (1994, *Proc. Natl. Acad. Sci., USA*, 91:3809-3813) and Schier et al (1996, *J. Mol. Biol.* 263:551-567).

All the above described techniques are known as such in the art and in themselves do not form part of the present invention. The skilled person will be able to use such techniques to provide specific binding members of the invention using routine methodology in the art.

A further aspect of the invention provides a method for obtaining an antibody antigen-binding domain specific for the synaptophysin epitope YPFRLHQVYFDAPSC (SEQ ID NO 9), the method comprising providing by way of addition, deletion, substitution or insertion of one or more amino acids in the amino acid sequence of a VH domain set out herein a VH domain which is an amino acid sequence variant of the VH domain, optionally combining the VH domain thus provided with one or more VL domains, and testing the VH domain or VH/VL combination or combinations for to identify a specific binding member or an antibody antigen binding domain specific for synaptophysin. Said VL domain may have an amino acid sequence which is substantially as set out herein.

An analogous method may be employed in which one or more sequence variants of a VL domain disclosed herein are combined with one or more VH domains.

A further aspect of the invention provides a method of preparing a specific binding member specific for synaptophysin, which method comprises:

(a) providing a starting repertoire of nucleic acids encoding a VH domain which either include a CDR3 to be replaced or lack a CDR3 encoding region;

(b) combining said repertoire with a donor nucleic acid encoding an amino acid sequence substantially as set out herein for a VH CDR3 such that said donor nucleic acid is inserted into the CDR3 region in the repertoire, so as to provide a product repertoire of nucleic acids encoding a VH domain;

(c) expressing the nucleic acids of said product repertoire;

(d) selecting a specific binding member specific for synaptophysin; and (e) recovering said specific binding member or nucleic acid encoding it.

Again, an analogous method may be employed in which a VL CDR3 of the invention is combined with a repertoire of nucleic acids encoding a VL domain which either include a CDR3 to be replaced or lack a CDR3 encoding region.

Similarly, one or more, or all three CDRs may be grafted into a repertoire of VH or VL domains which are then screened for a specific binding member or specific binding members specific for synaptophysin.

A substantial portion of an immunoglobulin variable domain will comprise at least the three CDR regions, together with their intervening framework regions. Preferably, the portion will also include at least about 50% of either or both of the first and fourth framework regions, the 50% being the C-terminal 50% of the first framework region and the N-terminal 50% of the fourth framework region. Additional residues at the N-terminal or C-terminal end of the substantial par of the variable domain may be those not normally associated with naturally occurring variable domain regions. For example, construction of specific binding members of the present invention made by recombinant DNA techniques may result in the introduction of N- or C-terminal residues encoded by linkers introduced to facilitate cloning or other manipulation steps. Other manipulation steps include the introduction of linkers to join variable domains of the invention to further protein sequences including immunoglobulin heavy chains, other variable domains (for example in the production of diabodies) or protein labels as discussed in more details below.

Although in a preferred aspect of the invention specific binding members comprising a pair of VH and VL domains are preferred, single binding domains based on either VH or VL domain sequences form further aspects of the invention. It is known that single immunoglobulin domains, especially VH domains, are capable of binding target antigens in a specific manner.

In the case of either of the single chain specific binding domains, these domains may be used to screen for complementary domains capable of forming a two-domain specific binding member able to bind synaptophysin.

This may be achieved by phage display screening methods using the so-called hierarchical dual combinatorial approach as disclosed in WO92/01047 in which an individual colony containing either an H or L chain clone is used to infect a complete library of clones encoding the other chain (L or H) and the resulting two-chain specific binding member is selected in accordance with phage display techniques such as those described in that reference. This technique is also disclosed in Marks et al, ibid.

Specific binding members of the present invention may further comprise antibody constant regions or parts thereof. For example, a VL domain may be attached at its C-terminal end to antibody light chain constant domains; including human Cκ Or Cλ chains, preferably Cκ chains. Similarly, a specific binding member based on a VH domain may be attached at its C-terminal end to all or part of an immunoglobulin heavy chain derived from any antibody isotype, e.g. IgG, IgA, IgE and IgM and any of the isotype sub-classes. Fc regions such as Δnab and Δnac as disclosed in WO99/58572 may be employed.

Specific binding members of the invention may be labelled with a detectable or functional label. Detectable labels include radiolabels such as $^{131}$I or $^{99}$Tc, which may be attached to antibodies of the invention using conventional chemistry known in the art of antibody imaging. Labels also include enzyme labels such as horseradish peroxidase. Labels further include chemical moieties such as biotin which may be detected via binding to a specific cognate detectable moiety, e.g. labelled avidin. Preferably the labels include fluorescent labels such as FITC.

Specific binding members of the present invention are designed to be used in methods of diagnosis or treatment in human or animal subjects, preferably human.

Accordingly, further aspects of the invention provide methods of diagnosis comprising administration of a specific binding member as provided, with one or more reagents e.g. conjugated to a detectable label such as FITC. The specific binding member as provided may be used in the development of a rapid and reliable test for liver fibrosis cells derived from biopsied tissue.

Further aspects of the invention provide methods of treatment comprising administration of a specific binding member as provided, pharmaceutical compositions comprising such a specific binding member, and use of such a specific binding member in the manufacture of a medicament for administration, for example in a method of making a medicament or pharmaceutical composition comprising formulating the specific binding member with a pharmaceutically acceptable excipient.

Clinical indications in which an antibody to hepatic stellate cells may be used to provide therapeutic benefit include any condition in which liver fibrosis has pathological consequences, for example in hepatic conditions such as viral infections e.g. Hepatitis and alcohol misuse. The specific binding member as provided may also be used in direct treatment of liver fibrosis via passive immunisation of human anti-stellate antibody or antibody like structures.

Anti-fibrotic treatment in accordance with the present invention may be used to provide clear benefit for patients with liver fibrosis. Anti-fibrotic treatment may be given by injection (e.g. intravenously) or by local delivery methods. The specific binding member as provided may be used to direct the delivery of pharmaceutical compositions to the target hepatic stellate cells.

Alternative formulation strategies may provide preparations suitable for oral or suppository route. The route of administration may be determined by the physicochemical characteristics of the treatment, by special considerations for the disease, to optimise efficacy or to minimise side-effects.

In accordance with the present invention, compositions provided may be administered to individuals. Administration is preferably in a "therapeutically effective amount", this being sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage etc, is within the responsibility of general practitioners and other medical doctors. Appropriate doses of antibody are well known in the art; see Ledermann J. A. et al. (1991) Int. J. Cancer 47: 659-664; Bagshawe K. D. et al. (1991) Antibody, Immunoconjugates and Radiopharmaceuticals 4: 915-922.

The precise dose will depend upon a number of factors, including whether the antibody is for diagnosis or for treatment, the size and location of the area to be treated, the precise nature of the antibody (e.g. whole antibody, fragment or diabody), and the nature of any detectable label or other molecule attached to the antibody. A typical antibody dose will be in the range 0.5 mg-1.0 g, and this may be administered as a bolus intravenously. Other modes of administration include intravenous infusion over several hours, to achieve a similar total cumulative dose. This is a dose for a single treatment of an adult patient, which may be proportionally adjusted for children and infants, and also adjusted for other antibody formats in proportion to molecular weight. Treatments may be repeated at daily, twice-weekly, weekly or monthly intervals, at the discretion of the physician.

A further mode of administration employs precoating of, or otherwise incorporation into, indwelling devices, for which the optimal amount of antibody will be determined by means of appropriate experiments.

An antibody molecule in some preferred embodiments of the invention is a monomeric fragment, such as F(ab) or scFv. Such antibody fragments may have the advantage of a relatively short half life.

Specific binding members of the present invention will usually be administered in the form of a pharmaceutical composition, which may comprise at least one component in addition to the specific binding member.

Thus pharmaceutical compositions according to the present invention, and for use in accordance with the present invention, may comprise, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. intravenous.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous injection, or injection at the site of affliction, the active ingredient will be in the form off a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

A composition may be administered alone or in combination with other treatments, either simultaneously or sequentially dependent upon the condition to be treated. Other treatments may include the administration of suitable doses of pain relief drugs such as non-steroidal anti-inflammatory drugs (e.g. asprin, ibuprofen or ketoprofen) or opiates such as morphine, or anti-emetics.

The present invention provides a method comprising causing or allowing binding of a specific binding member as provided herein to synaptophysin. As noted, such binding may take place in vivo, e.g. following administration of a specific binding member, or nucleic acid encoding a specific binding member, or it may take place in vitro, for example in ELISA, Western blotting, immunocytochemistry, immunoprecipitation or affinity chromatography.

The amount of binding of specific binding member to synaptophysin may be determined. Quantitation may be related to the amount of the antigen in a test sample, which may be of diagnostic interest.

The reactivities of antibodies on a sample may be determined by any appropriate means. Radioimmunoassay (RIA) is one possibility. Radioactive labelled antigen is mixed with unlabelled antigen (the test sample) and allowed to bind to the antibody. Bound antigen is physically separated from unbound antigen and the amount of radioactive antigen bound to the antibody determined. The more antigen there is in the test sample the less radioactive antigen will bind to the antibody. A competitive binding assay may also be used with non-radioactive antigen, using antigen or an analogue linked to a reporter molecule. The reporter molecule may be a fluorochrome, phosphor or laser dye with spectrally isolated absorption or emission characteristics. Suitable fluorochromes include fluorescein, rhodamine, phycoerythrin and Texas Red. Suitable chromogenic dyes include diaminobenzidine.

Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes which catalyse reactions that develop or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed.

The signals generated by individual antibody-reporter conjugates may be used to derive quantifiable absolute or relative data of the relevant antibody binding in samples (normal and test).

The present invention also provides the use of a specific binding member as above for measuring antigen levels in a competition assay, that is to say a method of measuring the level of antigen in a sample by employing a specific bind no member as provided by the present invention in a competition assay. This may be where the physical separation of bound from unbound antigen is not required. Linking a reporter molecule to the specific binding member so that a physical or optical change occurs on binding is one possibility. The reporter molecule may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding antibody and reporter molecule.

The present invention also provides for measuring levels of antigen directly, by employing a specific binding member according to the invention for example in a biosensor system.

The mode of determining binding is not a feature of the present invention and those skilled in the art are able to choose a suitable mode according to their preference and general knowledge.

The present invention further extends to a specific binding member which competes for binding to synaptophysin with any specific binding member which both binds the antigen and comprises a V domain including a CDR with amino acid substantially as set out herein or a V domain with amino acid sequence substantially as set out herein. Competition between binding members may be assayed easily in vitro, for example by tagging a specific reporter molecule to one binding member which can be detected in the presence of other untagged binding member(s), to enable identification of specific binding members which bind the same epitope or an overlapping epitope. Competition may be determined for example using ELISA or flow cytometry.

In testing for competition a peptide fragment of the antigen may be employed, especially a peptide including an epitope of interest. A peptide having the epitope sequence plus one or more amino acids at either end may be used. Such a peptide may be said to "consist essentially" of the specified sequence. Specific binding members according to the present invention may be such that their binding for antigen is inhibited by a peptide with or including the sequence given. In testing for this, a peptide with either sequence plus one or more amino acids may be used.

Specific binding members which bind a specific peptide may be isolated for example from a phage display library by panning with the peptide(s).

The present invention further provides an isolated nucleic acid encoding a specific binding member of the present invention. Nucleic acid includes DNA and RNA. In a preferred aspect, the present invention provides a nucleic acid which codes for a CDR, VH or VL domain of the invention as defined above.

The present invention also provides constructs in the form of plasmids, vectors, transcription or expression cassettes which comprise at least one polynucleotide as above.

The present invention also provides a recombinant host cell which comprises one or more constructs as above. A nucleic acid encoding any CDR, VH or VL domain, or specific binding member as provided itself forms an aspect of the present invention, as does a method of production of the encoded product, which method comprises expression from encoding nucleic acid therefor. Expression may conveniently be achieved by culturing under appropriate conditions recombinant host cells containing the nucleic acid. Following production by expression a VH or VL domain, or specific binding member may be isolated and/or purified using any suitable technique, then used as appropriate.

Specific binding members, VH and/or VL domains, and encoding nucleic acid molecules and vectors according to the present invention may be provided isolated and/or purified, e.g. from their natural environment, in substantially pure or homogeneous form, or, in the case of nucleic acid, free or substantially free of nucleic acid or genes origin other than the sequence encoding a polypeptide with the required function. Nucleic acid according to the present invention may comprise DNA or RNA and may be wholly or partially synthetic. Reference to a nucleotide sequence as set out herein encompasses a DNA molecule with the specified sequence, and encompasses a RNA molecule with the specified sequence in which U is substituted for T, unless context requires otherwise.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, NS0 mouse melanoma cells, YB2/0 rat myeloma cells and many others. A common, preferred bacterial host is *E. coli*.

The expression of antibodies and antibody fragments in prokaryotic cells such as *E. coli* is well established in the art. For a review, see for example Plückthun, A. Bio/Technology 9: 545-551 (1991). Expression in eukaryotic cells in culture is also available to those skilled in the art as an option for production of a specific binding member, see for recent reviews, for example Ref, M. E. (1993) Curr. Opinion Biotech. 4: 573-576; Trill J. J. et al. (1995) Curr. Opinion Biotech 6: 553-560.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. 'phage, or phagemid, as appropriate. *Molecular Cloning: a Laboratory Manual:* 3rd edition, Sambrook and Russell, 2001, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in *Current Protocols in Molecular Biology*, Second Edition, Ausubel et al. eds., John Wiley & Sons, 1992.

Thus, a further aspect of the present invention provides a host cell containing nucleic acid as disclosed herein. A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage.

The introduction may be followed by causing or allowing expression from the nucleic acid, e.g. by culturing host cells under conditions for expression of the gene.

In one embodiment, the nucleic acid of the invention is integrated into the genome (e.g. chromosome) of the host cell.

Integration may be promoted by inclusion of sequences which promote recombination with the genome, in accordance with standard techniques.

The present invention also provides a method which comprises using a construct as stated above in an expression system in order to express a specific binding member or polypeptide as above.

Aspects and embodiments of the present invention will now be illustrated by way of example with reference to the following experimentation.

All documents cited anywhere in this specification are incorporated by reference.

MATERIALS AND METHODS

Conjugation of Peptides Bovine Serum Albumin

Figure 1:
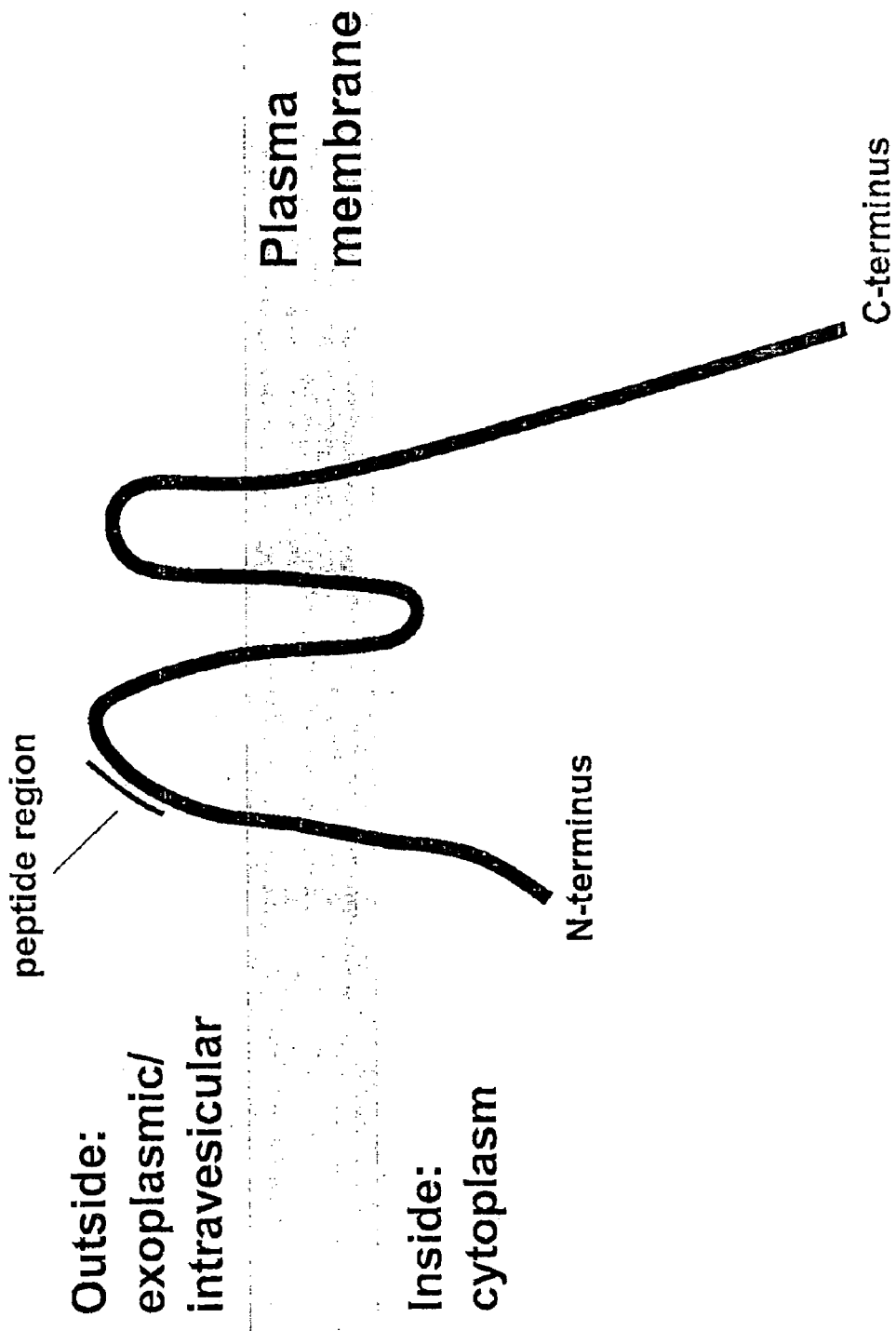
FIG. 1

The peptide YPFRLHQVYFDAPSC (SEQ ID NO 9) corresponding to amino acids present on the exoplasmic side of the synaptophysin protein (FIG. 1) was synthesized using Fmoc chemistry (Proteomics Group, University of Aberdeen) and was judged pure by HPLC. The molecular weight of the peptide was checked by mass spectrometry (data not shown). The peptide was chemically conjugated to bovine serum albumin (BSA) using 3 maleimidoacetic acid N-hydroxysuccinimide (MBS) (Leel V. et al. Biochem Biophys Res Commun 2004; 316: 872-7). SDS-PAE and mass spectrometry analyses (MALDI-TOF, Applied Biosystems Voyager-DE STR) confirmed that the peptides had been conjugated to BSA—typically on average ~4 peptide molecules per molecule of albumin (data not shown).

Phage Display Generation of a Soluble Single-Chain Antibody Fragment (scAb) to Peptide Sequences The human single-fold scFv phagemid (pIT2) libraries (Tomlinson I+J, MRC, UK) were used to screen for phage-antibodies with specificity for the peptide sequence essentially as outlined in Leel V. et al. Biochem Biophys Res Commun 2004; 316:872-7. A total of three rounds of panning were carried out against the peptide sequence. The pans were conducted in 4 ml PBS (137 mM NaCl, 2.7 mM KCl, 10 mM phosphate pH 7.4) containing 2% (w/v) dried milk (MPBS) and 2 mg/ml BSA to increase the ratio of phage-antibodies with specificity for peptides versus BSA.

Anti-Peptide Phage-Antibody ELISA

Purified polyclonal phage enriched for binders to peptides were assayed by ELISA using flat bottomed 96-well Immulon-4 microtitre plates (Dynex, Sussex, UK) coated with 2 μg/well protein (peptide-BSA or BSA) in PBS overnight at 4° C. Bound phage were detected by incubation with 100 μl/well horseradish peroxidase (HRP) conjugated anti-M13 antibody (AmershamPharmacia) for 1 h, washing, and incubation with 100 μl/well tetramethylbenzidine dihydrochloride solution (KPL Laboratories, Gaithersburg, Md.). Reactions were stopped with 50 μl/well 1M $H_2SO_4$, and the absorbance at 450 nm read using a microtitre plate reader.

Identification of Monoclonal Phage-Antibodies to Peptides and Subcloning into the Expression Vector pIMS147

Individual colonies from pan 3 were grown in 96 well plates (Greiner) and phage-antibodies rescued with M13 KO7.

Specificity of phage supernatants for binding to peptide-BSA and BSA alone was determined by ELISA. The scFv encoding regions of positive clones were subcloned in to the expression vector pIMS147. This is a modification of the IPTG (isopropyl-β-D-thiogalactopyranoside) inducible pUC based vector pIMS100 (Hayhurst A. et al. Protein Expr Purif 1999; 15:336-43). The addition of a hexa-histidine tag permits purification of the expressed scAb by immobilised metal ion chelate affinity chromatography. Vectors were transformed into E. coli TG1 or XL1 blue cells.

Expression, Purification and Characterization of scAbs

The scAb was expressed in IPTG-treated cells as outlined in Leel V. et al. Biochem Biophys Res Commun 2004; 316: 872-7 and purified via the hexa-histidine C-terminal tag tail using $Ni^{2+}$ charged IMAC Fast Flow Sepharose resin (AmershamPharmacia) according to manufacturer's instructions. After extensive dialysis at 4° C. against PBS scAb was stored at −20° C. The purified scAb was quantified by capture ELISA via the human Cκ domain using a whole human IgG assay standard as outlined in Leel V. et al. Biochem Biophys Res Commun 2004; 316:872-7.

Expressed Purified Anti-Peptide scAb ELISA

Expressed scAb was tested for its ability to interact with peptide by ELISA essentially as outlined for polyclonal anti-peptide phage-antibody ELISAs. Bound scAb was detected horseradish peroxidase conjugated anti-human Cκ light chain antibody (Sigma Chem. Co. Poole, UK).

SDS-PAGE and Western Blotting

Western blotting was performed essentially as described in Wright M. C. et al. Mol Pharmacol 1996; 50:856-63.

FITC Labelling of Proteins

ScAbs were fluorescently labelled using the Fluoroporter FITC protein labelling kit (Molecular Probes) according to the manufacturer's instructions. This methodology was also employed to conjugate C1-3 scab with tributyl tin using tributyl tin isothiocyanate (Aldrich Chemicals, Poole, UK).

Animals and Cell Preparation

Human hepatocytes were obtained from the UK Human Tissue Bank (DeMontfort University, Leicester, UK). Human HSCs were isolated from margins of normal liver tissue that was removed from patients due to the presence of a tumour. The use of human tissue in these studies was authorised by the Grampian Regional Ethics Committee and included full donor consent. Protocols for human liver cell culture have been published in Wright M. C. et al, Hum Exp Toxicol 1996; 15:203-4, and Harvey J. L. et al. Drug Metab Dispos 2000; 28:96-101. Protocols for rat HSC and B-13 cell culture have been published in Wright M. C. et al. Gastroenterology 2001; 121:685-98, and Marek C. J. et al. Biochem J 2003; 370:763-9.

Incubation of FITC-Labelled scAb with Cells

FITC-C1-3 scAb was tested for its ability to interact with hepatic stellate cells in culture by fluorescence microscopy. Human hepatic stellate cells were seeded ($1 \times 10^3$ cells per chamber) on chamber slides (Nunclon, Naperville) in complete medium prior to experimentation. Cells were washed twice in phosphate buffered saline (PBS) and incubated in 500 μl Hepes/HBSS buffer (0.14M NaCl, 5.4 mM KCl, 0.34 mM $Na_2HPO_4$, 0.94 mm $KH_2PO_4$, 5.6 mM glucose, 1 mM $CaCl_2$, 6 mM HEPES, 4 mM $NaHCO_3$ pH7.4) containing 10 μg scAb or FITC-C1-3 scAb for 1 h at room temperature in the dark. The cells were then washed in PBS and mounted with Vectashield mounting medium (Vector laboratories, Burlingame, Calif.) containing 4',6' diamindino-2 phenylindole (DAPI) to stain cell nuclei and coverslips applied. Florescence microscopy was carried out using a Zeiss Axeola II microscope with a Photometrics Sensis camera, and data captured using the Smart Capture programme. Human hepatocytes (UK Human Tissue Bank) were originally cultured in a collagen-coated 24 well plate ($1 \times 10^5$/well) and maintained in William's medium E supplemented with 80 units/ml penicillin and 80 μg/ml streptomycin.

For co-culture experiments, hepatic stellate cells were seeded into hepatocytes cultures ($1\times10^3$ cells per well) and cultured for 24 h prior to experimentation. The C1-3 or FITC-C1-3 scAb was incubated as outlined for pure hepatic stellate cell cultures except that after 1 hour incubation and washing, the cells were harvested by trypsinisation and centrifugation at 1000 rpm for 5 min. The cell pellet was then resuspended in 0.4% formaldehyde/$10^6$ cells, applied onto glass slides by cytocentrifugation and mounted with Vectashield containing DAPI. Slides were viewed by fluorescence microscopy as before.

Fluorescence microscopy without cell fixation was used to compare the effects of peptides and monensin on FITC-C1-3 binding to HSCs since DAPI staining masked nuclear FITC-C1-3 staining. HSCs seeded into 24 well plates were washed with Hepes/HBSS and then incubated at 37° C. in 500 μl/well Hepes/HBSS containing 10 μg scAb with or without additional compounds. After 1 hour, the cells were washed 3 times with 500 μl Hepes/HBSS. Cells were analysed using an Axiovert 100 microscope (Zeiss, Germany) using filter set #9 (BP 450-490 nm; LP 515 nm).

FACS Analysis

FITC-C1-3 scAb was added to culture medium (200 μg/10 mls) and incubated with a confluent (10 cm diameter dish) culture of HSCs for 1 hour at 37° C. The medium was then removed and the cells were washed in PBS. The cells were then detached from the culture substratum non-enzymatically using cell dissociation solution (Sigma, Poole, UK), pelleted by centrifugation and fixed/permeabilised using BD cytofix/cytoperm (BD Biosciences, Oxford, UK). After 15 minutes, the cells were washed in 0.5 mls 1× wash/perm buffer (BD Biosciences, Oxford, UK) and incubated with a mouse anti-α-smooth muscle actin monoclonal antibody (Sigma, Poole, UK) diluted in 1× wash/perm buffer. Cells were then washed in 1× wash/perm buffer and incubated with a biotin-conjugated anti-mouse-IgG (1:200, DakoCytomatron, Cambridgeshire, UK) for 30 minutes on ice, washed twice and then incubated with a streptavadin-allophycocyanin (APC) conjugate (1:200, BD Biosciences, Oxford, UK) for 30 minutes on ice. The cells were analysed by flow cytometry (LSR I, BD, Oxford, UK). Non-specific flouorescence was controlled by incubation of the cells with isotype-specific control antibodies.

RESULTS

The technique of phage display was used to pan for recombinant phage antibodies from the Tomlinson I+J libraries with affinity for the target peptide YPFRLHQVYFDAPSC (SEQ ID NO 9). FIG. 2 shows that phage-antibodies with affinity for the target peptide were selectively bound to immunotubes and amplified through 3 separate pans. Ninety six separate clones from the third pan library were individually screened for phage-antibody binding to BSA and target peptide-BSA. Fifty seven clones demonstrated a high affinity for target peptide-BSA, none of the clones demonstrated any affinity for BSA in this assay (data not included). The 12 clones that gave the highest response in the monoclonal phage-antibody ELISA were selected and the scab encoding region sequenced.

Figure 3:
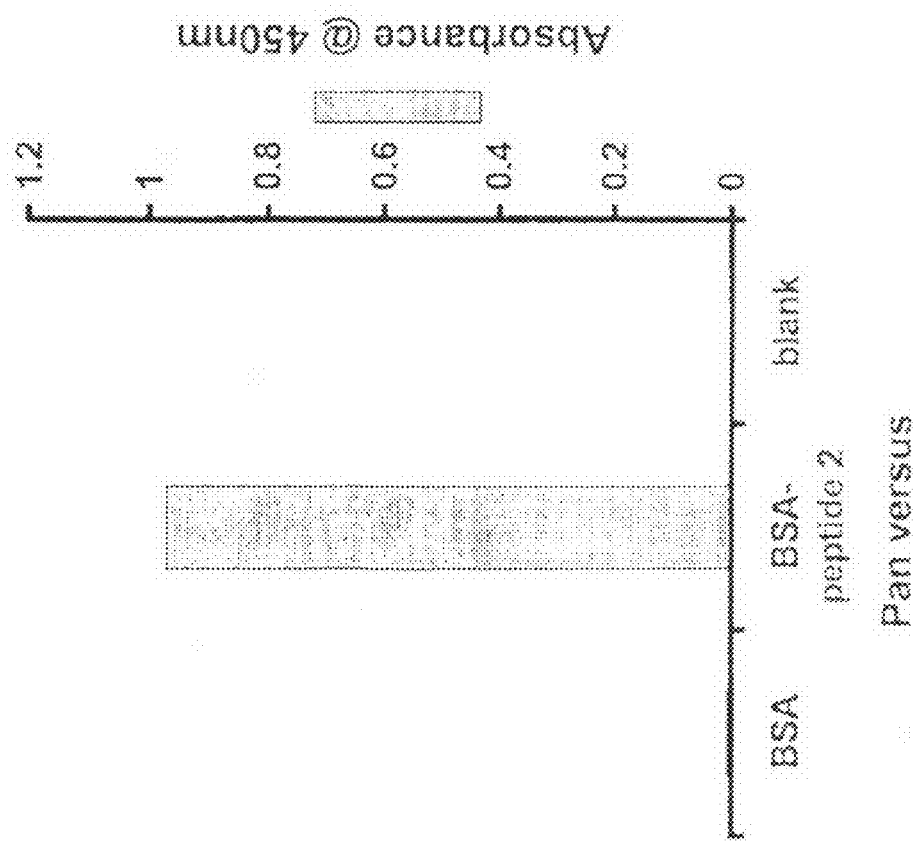
Figure 6:
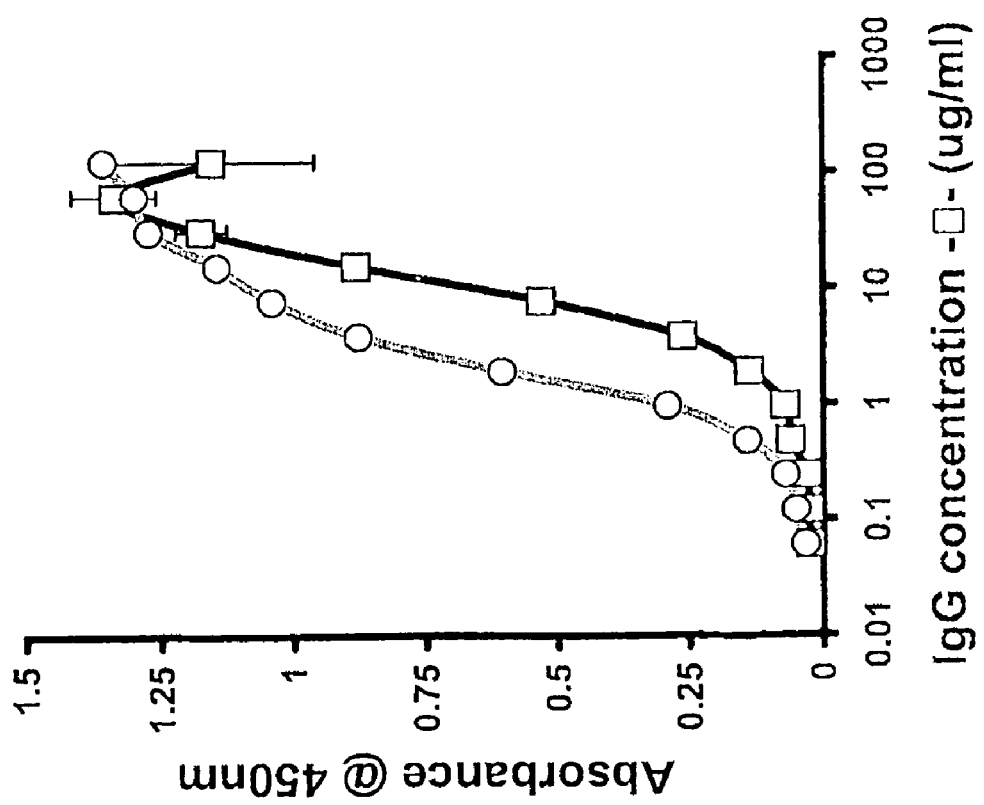
Figure 7:
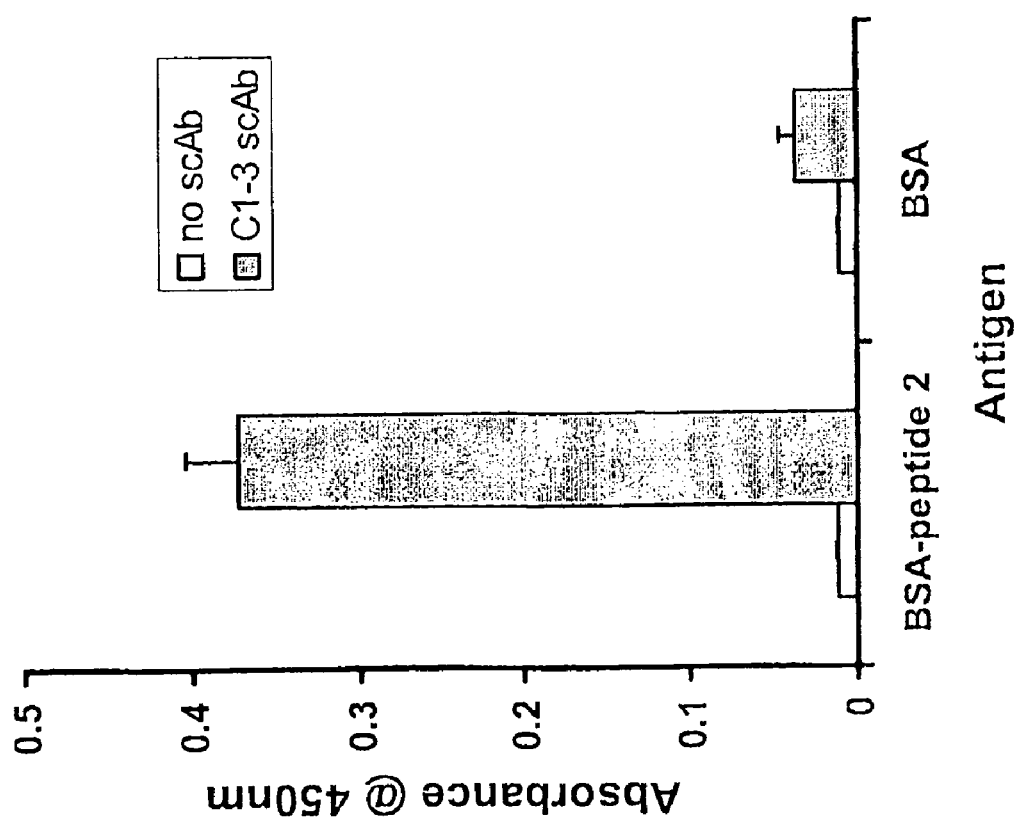
Figure 8:
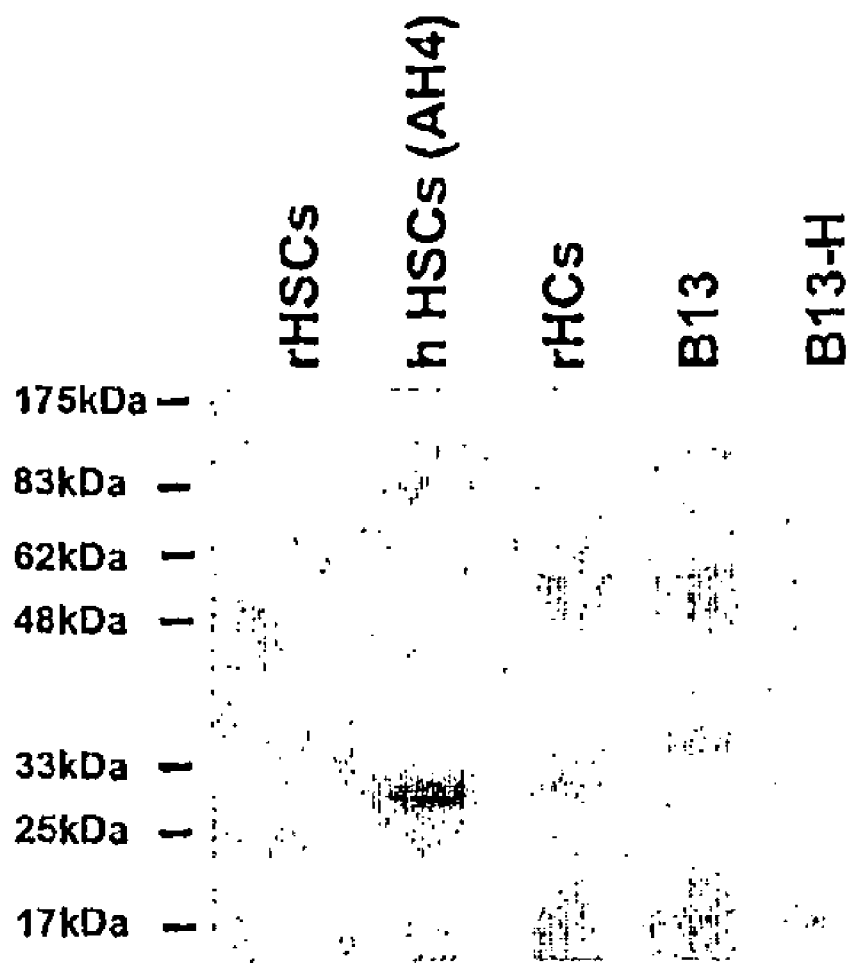

Sequencing indicated that many contained in-frame stop codons within the coding region of the scAb. Constructs were sub-cloned into pIMS147 and transformed into an *E. coli* strain containing suppressor tRNAs (i.e. TG-1). Although these constructs generated scAbs in TG-1s with high affinity for the peptide, high levels of scAb expression was not obtained (data not shown). Phage antibody clone C1 however, did not contain a stop codon within the scAb encoding region and gave a good binding response in the monoclonal phage-antibody ELISA screen (FIG. 3). Clone C1 was subcloned into pIMS147 vector and transformed into XL-1 blue *E coli*. Clone pIMS147 C1-3 (FIG. 4) directed a high level of scAb expression (FIG. 5) that specifically recognised the peptide in an ELISA (FIG. 6). An ELISA assay for expressed scAb confirmed the generation of an scAb that was specific for the peptide YPFRLHQVYFDAPSC (SEQ ID NO 9). FIG. 7 indicates that approximately 8 times more expressed scab bound to peptide-BS (i.e. YPFRLHQVYFDAPSC-BSA, SEQ ID NO 9-BSA) than to BSA alone. Binding of a control, lacking the scAb, to either peptide-BSA or BSA was minimal. Western analysis versus several different cell type extracts demonstrated that the C1-3 scAb binds to a protein of ~32 kDa in human HSCs, the predicted size of the Human antibody targeting of HSCs 12 non-glycosylated synaptophysin protein (Eastwood S. L. et al. Brain Res Bull 2001; 55: 569-78). Interestingly, the C1-3 scAb did not cross-react with synaptophysin in rat HSCs (FIG. 8).

Figure 9:
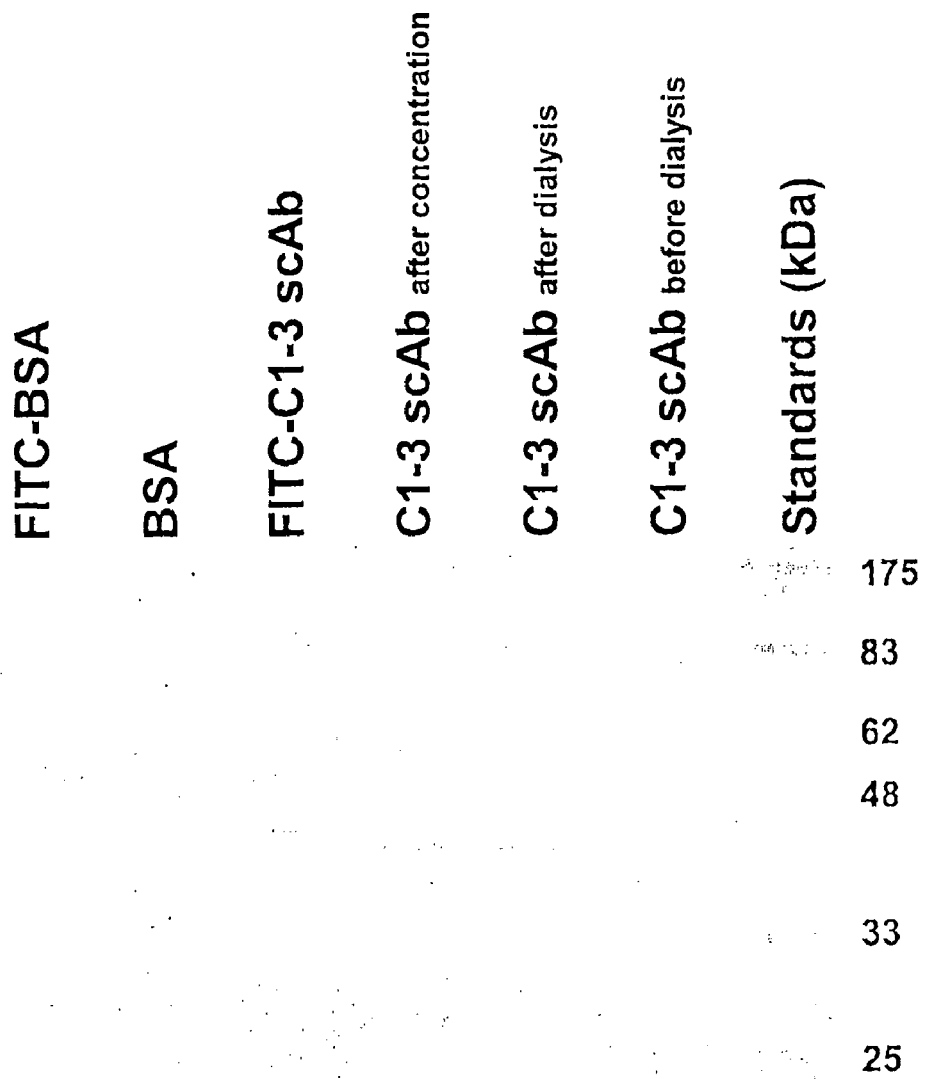

In order to determine if the C1-3 scAb is able to bind to the surface of live HSCs C1-3 scAb was labelled with FITC and confirmed by SDS-PAGE as shown in FIG. 9 as judged by a decrease in the migration of FITC-C1-3 scAb. C1-3 scab before and after dialysis and after concentration had a MW of approximately 40 Kda. C1-3 scAb labelled with FITC has a MW of approximately 45 Kda.

Figure 10:
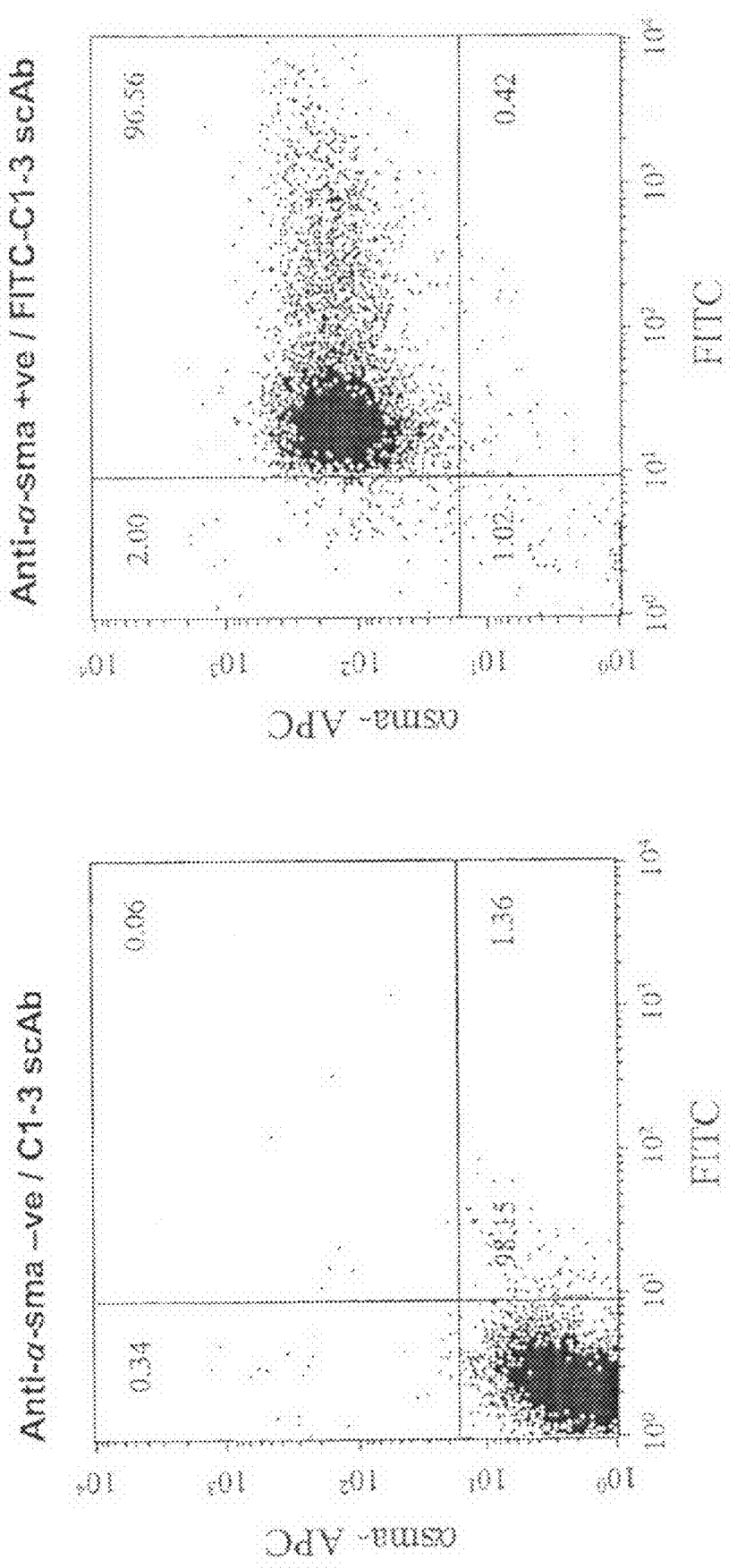
Figure 11:
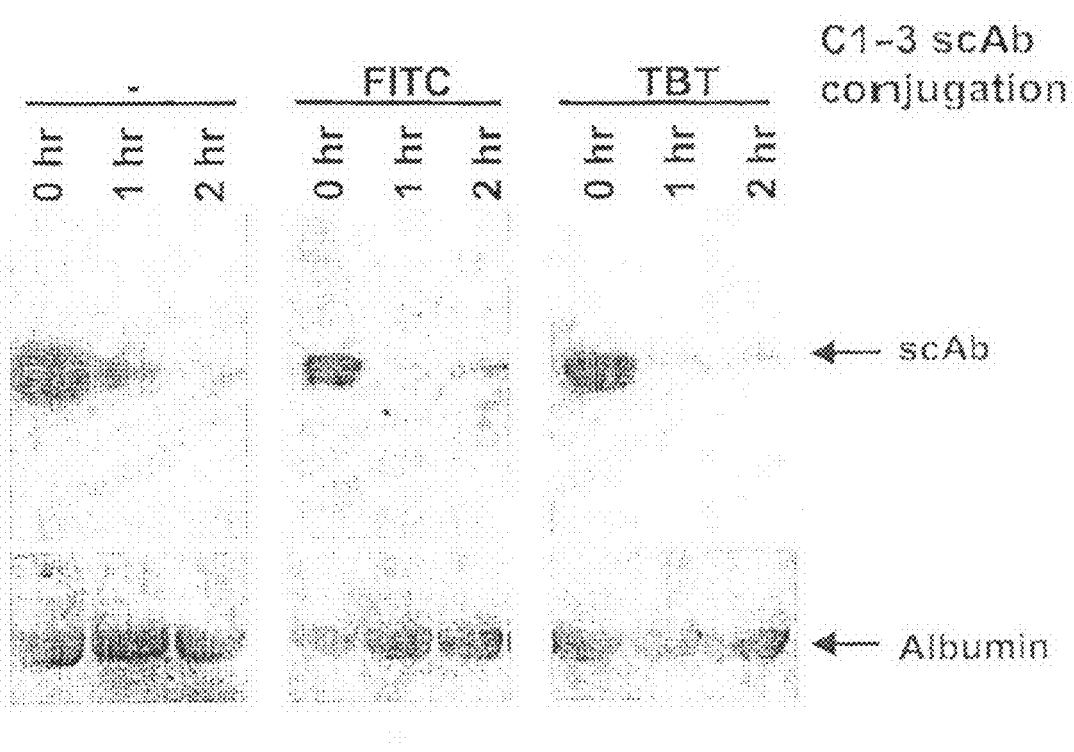
Figure 12:
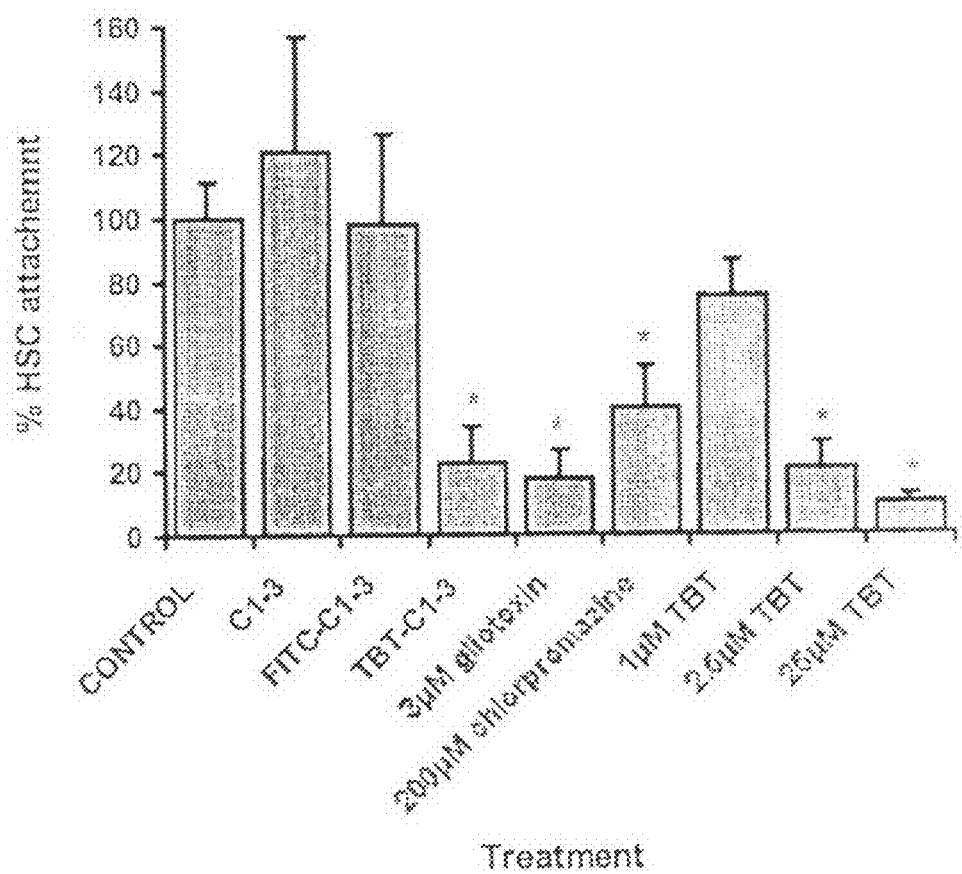

FITC-C1-3 scAb was then added to activated human HSCs in culture. Immunocytochemical staining (not shown) and FACS analysis of human HSC cultures demonstrate that cells were exclusively α-smooth muscle actin positive and were therefore activated HSCs and/or liver-derived myofibroblasts (both cell types are believed to contribute to fibrogenesis (Ramadori G. et al. Liver 2002; 22:283-94)—see FIG. 10). Co-staining cells with FITC-C1-3 under native conditions prior to fixing demonstrated that all the cells bound C1-3 scAb, although there was a greater variation in the intensity of FITC-C1-3 staining compared to α-smooth muscle actin (FIG. 10). This suggests that there may be a sub-population of α-smooth muscle actin-expressing cells with a higher level of synaptophysin and/or more avid FITC-C1-3 scAb uptake mechanism. The association of C1-3, FITC-C1-3 or tributyl-tin-conjugated C1-3 scAb (TBT-C1-3) with HSCs corresponded with a reduction in culture medium concentrations (FIG. 11). There was no evidence of toxicity with C1-3 or FITC-C1-3 in contrast to compounds known to kill HSCs by either apoptosis (gliotoxin) or necrosis (chlorpromazine) (see FIG. 12). Interestingly, TBT-C1-3 scAb was toxic to HSCs, suggesting that C1-3 scAbs are internalised and that it is possible to conjugate drugs to C1-3 and retain drug pharmacology.

Fluorescence experiments suggest that the FITC-C1-3 scAb specifically interacts with hepatic stellate cells in culture since green (fluorescein-associated) fluorescence was associated with hepatic stellate cells incubated with FITC-C1-3 scAb. Using a mounting medium that inhibited photobleaching and stained nuclei blue it was found that in most cases, fluorescence was located around the nuclear and cell membranes. Staining often appeared punctate, that may reflect association with localised structures. In this respect, it is known that synaptophysin is concentrated at the synaptic vesicles in neurones where it forms homoligomers of variable subunit numbers. Staining was also observed around the nuclear membrane supporting the suggestion that C1-3 scAb is subjected to intracellular accumulation. No detectable green fluorescence was observed in hepatic stellate cell cultures incubated with (fluorescein un-conjugated) C1-3 scAb. To determine the specificity of the interaction between C1-3 scAb and hepatic stellate cells, human hepatocytes were also incubated with FITC-C1-3 scAb. Hepatocytes incubated with either C1-3 scAb or FITC-C1-3 scAb showed no associated green fluorescence suggesting that the C1-3 scAb antibody does not bind to hepatocytes. To further test the ability of the C1-3 scAb to differentiate between cell types, hepatic stellate cell and hepatocytes were co-cultured and incubated with FITC-C1-3 scAb. Fluorescence was observed on stellate cells whilst hepatocytes consistently failed to display detectable levels of associated green fluorescence. No significant green fluorescence was observed in experiments where co-cultures were incubated with (fluorescein un-conjugated) C1-3 scAb. The specificity of action of the C1-3 scAb for binding to hepatic stellate cells was examined using FITC labelled BSA. Both human hepatic stellate cells and hepatocytes were incubated with BSA and FITC-BSA. Both human HSCs and hepatocytes displayed cytoplasmic foci of fluorescence when incubated with FITC-BSA suggesting that it was not the presence of fluorescein on proteins (i.e. C1-3) non-specifically preventing C1-3 scAb uptake into hepatocytes but that the C1-3 scAb did not interact with hepatocytes. Fluorescence binding was not detected in COS-7 or HepG2 cells when incubated with C1-3scAb or C1-3scAb-FITC.

Figure 13:
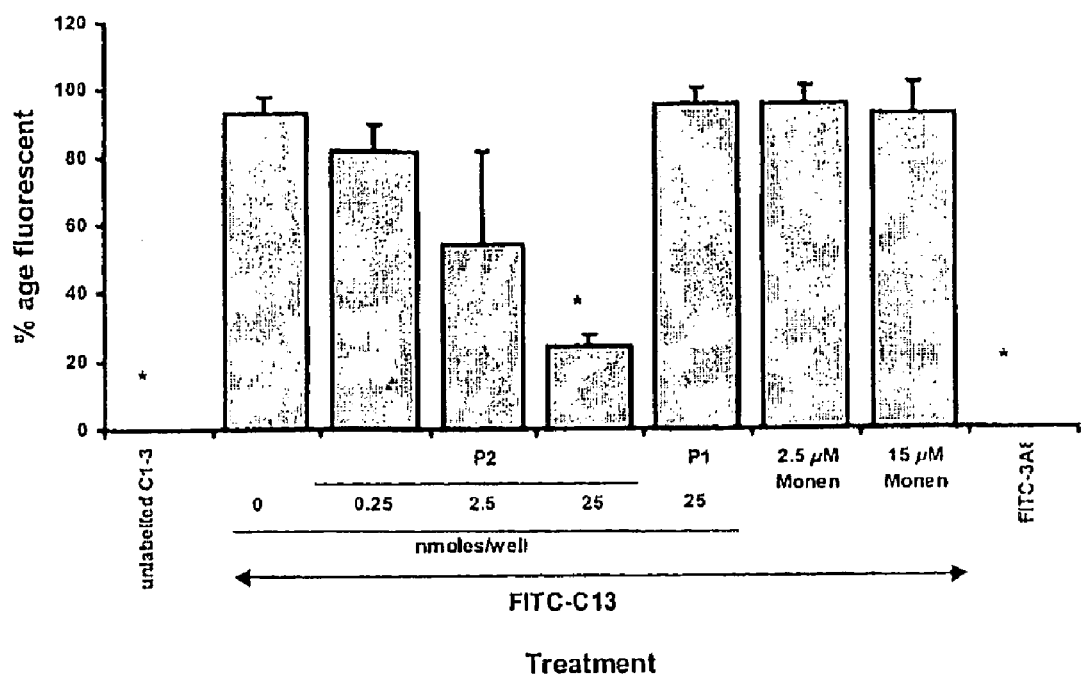

Fluorescence microscopy without fixation and DAPI co-staining prior to examination was used to compare the effects of peptides or monensin on FITC-C1-3 HSC binding/uptake. FIG. 13 shows that FITC-C1-3 scAb associated with HSCs in contrast to a control FITC-labelled 3A8 scAb (previously prepared to the toxin microcystin (McElhiney J. et al., Appl Environ Microbiol 2002; 68: 5288-95). Addition of the peptide ATDPENIIKEMPMC (SEQ ID NO 27), corresponding to other amino acids present on the exoplasmic side of the synaptophysisn protein to the cultures did not significantly inhibit FITC-C1-3 association with HSCs whereas the target peptide YPFRLHQVYFDAPSC (SEQ ID NO 9) decreased FITC-C1-3 binding to HSCs in a dose-dependent manner. Addition of the endocytosis inhibitor monensin did not inhibit the total number of cells stained with FITC-C13 but reduced uptake as indicated by a loss of nuclear FITC-C1-3 staining.

Figure 14:
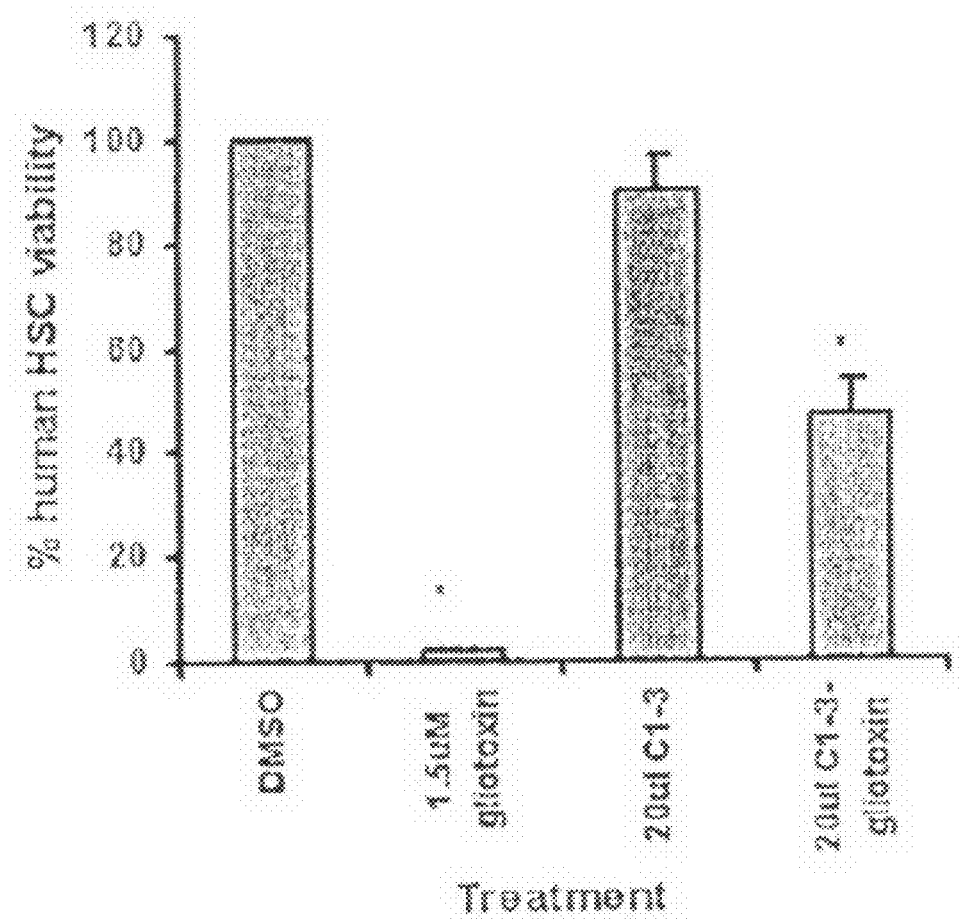

C1-3 scAb at a concentration of 1 mg/ml was conjugated with gliotoxin essentially as described by Fox et al. J Microbiol Methods 2004; 56:221-230. SDS-PAGE confirmed that the protein had been modified (data not shown). An antibody to gliotoxin (obtained from Fox et al.) confirmed that gliotoxin had been covalently attached to the C1-3 scAb. MALDI-TOF analysis indicated that the mass of the protein had been increased most commonly by 1683 daltons. Taking into account conjugation procedure, suggests most C1-3 proteins are conjugated with 4 molecules of gliotoxin. FIG. 14 shows that Gliotoxin killed human HSCs, and C1-3 conjugated with gliotoxin also killed HSCs. This data indicates that it is possible to conjugate a drug to the C1-3 scAb and retain targeting and drug efficacy.

```
SEQ ID NO 1:
    NcoI
    CC ATG GCC GAA GTG CAG CTG TTG GAG TCT GGG GGA GGC TTG GTA

CAG CCT GGG GGG TCC CTG AGA CTC TCC TGT GCA GCC TCT GGA
                                  HCDR1              HFW2
       TTC ACC TTT AGC AGC TAT GCC ATG AGC TGG GTC CGC CAG GCT
                                                    HCDR2
       CCA GGG AAG GGG CTG GAG TGG GTC TCA ACT ATT GCT GCG TCG
                                                          HFW3
       GGT CCT TCT ACA GGG TAC GCA GAC TCC GTG AAG GGC CGG TTC

ACC ATC TCC AGA GAC AAT TCC AAG AAC ACG CTG TAT CTG CAA

ATG AAC AGC CTG AGA GCC GAG GAC ACG GCC GTA TAT TAC TGT
                          HCDR3                     HFW4
       GCG AAA ACT ACG GCG AAG TTT GAC TAC TGG GGC CAG GGA ACC

CTG GTC ACC GTC TCG AGC

SEQ ID NO 2:
      1 Met Ala Glu Val Gln Leu Leu Glu Ser Gly Gly Gly Leu Val

15 Gln Pro Gly Gly Ser Leu Arg Leu Ser Cys Ala Ala Ser Gly
                              HCDR1              HFW2
     30 Phe Thr Phe Ser Ser Tyr Ala Met Ser Trp Val Arg Gln Ala
                                                    HCDR2
     45 Pro Gly Lys Gly Leu Glu Trp Val Ser Thr Ile Ala Ala Ser
                                                          HFW3
     60 Gly Pro Ser Thr Gly Tyr Ala Asp Ser Val Lys Gly Arg Phe

75 Thr Ile Ser Arg Asp Asn Ser Lys Asn Thr Leu Tyr Leu Gln

90 Met Asn Ser Leu Arg Ala Glu Asp Thr Ala Val Tyr Tyr Cys
                          HCDR3                     HFW4
    105 Ala Lys Thr Thr Ala Lys Phe Asp Tyr Trp Gly Gln Gly Thr

120 Leu Val Thr Val Ser Ser
```

-continued

SEQ ID NO: 3

ACG GAC ATC CAG ATG ACC CAG TCT CCA TCC TCC CTG TCT GCA

TCT GTA GGA GAC AGA GTC ACC ATC ACT TGC CGG GCA AGT CAG
                                   LCDR1                                      LFW2
AGC ATT AGC AGC TAT TTA AAT TGG TAT CAG CAG AAA CCA GGG
                                                                  LCDR2
AAA GCC CCT AAG CTC CTG ATC TAT TCT GCA TCC CGA TTG CAA
                                  LFW3
AGT GGG GTC CCA TCA AGG TTC AAT GGC AGT GGA TCT GGG ACA

GAT TTC ACT CTC ACC ATC AGC AGT CTG CAA CCT GAA GAT TTT
                                      LCDR3
GCA ACT TAC TAC TGT CAA CAG CTG CAG AGG AAG CCT ACG ACG
                                                                     notI
TTC GGC CAA GGG ACC AAG GTG GAA ATC AAA CGG <u>GCG GCC GCT</u>

GCA

SEQ ID NO: 4

Thr Asp Ile Gln Met Thr Gln Ser Pro Ser Ser Leu Ser Ala

Ser Val Gly Asp Arg Val Thr Ile Thr Cys Arg Ala Ser Gln
               LCDR1                      LFW2
Ser Ile Ser Ser Tyr Leu Asn Trp Tyr Gln Gln Lys Pro Gly
                                              LCDR2
Lys Ala Pro Lys Leu Leu Ile Tyr Ser Ala Ser Arg Leu Gln
                                  LFW3
Ser Gly Val Pro Ser Arg Phe Asn Gly Ser Gly Ser Gly Thr

Asp Phe Thr Leu Thr Ile Ser Ser Leu Gln Pro Glu Asp Phe
                                    LCDR3
Ala Thr Tyr Tyr Cys Gln Gln Leu Gln Arg Lys Pro Thr Thr
                                                        notI
Phe Gly Gln Gly Thr Lys Val Glu Ile Lys Arg <u>Gly Ala Ala</u>

Ala

SEQ ID NO: 5
GGT GGA GGC GGT TCA GGC GGA GGT GGC AGC GGC GGT GGC GGG TCG

SEQ ID NO: 6
Gly Gly Gly Gly Ser Gly Gly Gly Gly Ser Gly Gly Gly Gly Ser

SEQ ID NO: 7

<u>CC ATG GCC</u> GAA GTG CAG CTG TTG GAG TCT GGG GGA GGC TTG GTA

CAG CCT GGG GGG TCC CTG AGA CTC TCC TGT GCA GCC TCT GGA
                                                   HCDR1                     HFW2
TTC ACC TTT AGC AGC TAT GCC ATG AGC TGG GTC CGC CAG GCT
                                                                    HCDR2
CCA GGG AAG GGG CTG GAG TGG GTC TCA ACT ATT GCT GCG TCG

GGT CCT TCT ACA GGG TAC GCA GAC TCC GTG AAG GGC CGG TTC

ACC ATC TCC AGA GAC AAT TCC AAG AAC ACG CTG TAT CTG CAA

ATG AAC AGC CTG AGA GCC GAG GAC ACG GCC GTA TAT TAC TGT
                            HCDR3                        HFW4
GCG AAA ACT ACG GCG AAG TTT GAC TAC TGG GGC CAG GGA ACC

CTG GTC ACC GTC TCG AGC <u>GGT GGA GGC GGT TCA GGC GGA GGT</u>
                                                                            Linker
<u>GGC AGC GGC GGT GGC GGG TCG</u> ACG GAC ATC CAG ATG ACC CAG TCT CCA TCC TCC CTG TCT GCA TCT GTA GGA GAC AGA GTC ACC
                                                                   LCDR1
ATC ACT TGC CGG GCA AGT CAG AGC ATT AGC AGC TAT TTA AAT
    LFW2
TGG TAT CAG CAG AAA CCA GGG AAA GCC CCT AAG CTC CTG ATC
                                LCDR2                      LFW3
TAT TCT GCA TCC CGA TTG CAA AGT GGG GTC CCA TCA AGG TTC AAT GGC AGT GGA TCT GGG ACA GAT TTC ACT CTC ACC ATC AGC
                                                                      LCDR3
AGT CTG CAA CCT GAA GAT TTT GCA ACT TAC TAC TGT CAA CAG

CTC CAG AGG AAG CCT ACG ACG TTC GGC CAA GGG ACC AAG GTG
                           notI
GAA ATC AAA CGG <u>GCG GCC GCT</u> GCA CCA <u>TCT GTC TTC ATC TTT</u>

<u>. . . . . .</u>            Ck - light chain + his tag

-continued

SEQ ID NO: 8

```
  1 Met Ala Glu Val Gln Leu Leu Glu Ser Gly Gly Gly Leu Val
 15 Gln Pro Gly Gly Ser Leu Arg Leu Ser Cys Ala Ala Ser Gly
                           HCDR1              HFW2
 30 Phe Thr Phe Ser Ser Tyr Ala Met Ser Trp Val Arg Gln Ala
                                         HCDR2
 45 Pro Gly Lys Gly Leu Glu Trp Val Ser Thr Ile Ala Ala Ser
                                                     HFW3
 60 Gly Pro Ser Thr Gly Tyr Ala Asp Ser Val Lys Gly Arg Phe
 75 Thr Ile Ser Arg Asp Asn Ser Lys Asn Thr Leu Tyr Leu Gln
 90 Met Asn Ser Leu Arg Ala Glu Asp Thr Ala Val Tyr Tyr Cys
                      HCDR3                HFW4
105 Ala Lys Thr Thr Ala Lys Phe Asp Tyr Trp Gly Gln Gly Thr
120 Leu Val Thr Val Ser Ser Gly Gly Gly Gly Ser Gly Gly Gly
                                                      Linker
135 Gly Ser Gly Gly Gly Gly Ser Thr Asp Ile Gln Met Thr Gln
150 Ser Pro Ser Ser Leu Ser Ala Ser Val Gly Asp Arg Val Thr
                                    LCDR1
165 Ile Thr Cys Arg Ala Ser Gln Ser Ile Ser Ser Tyr Leu Asn
180 Trp Tyr Gln Gln Lys Pro Gly Lys Ala Pro Lys Leu Leu Ile
195 Tyr Ser Ala Ser Arg Leu Gln Ser Gly Val Pro Ser Arg Phe
210 Asn Gly Ser Gly Ser Gly Thr Asp Phe Thr Leu Thr Ile Ser
225 Ser Leu Gln Pro Glu Asp Phe Ala Thr Tyr Tyr Cys Gln Gln
240 Leu Gln Arg Lys Pro Thr Thr Phe Gly Gln Gly Thr Lys Val
                          notI
255 Glu Ile Lys Arg Gly Ala Ala Ala Pro Ser Val Phe Ile Phe
    ...                         Ck - light chain + his tag
```

SEQ ID NO: 9

YPFRLHQVYFDAPSC

SEQ ID NO 10:

AGC TAT GCC ATG AGC
Ser Tyr Ala Met Ser

SEQ ID NO 11:

ACT ATT GCT GCG TCG GGT CCT TCT ACA GGG TAC GCA GAC TCC
Thr Ile Ala Ala Ser Gly Pro Ser Thr Gly Tyr Ala Asp Ser
GTG AAG GGC
Val Lys Gly

SEQ ID NO 12:

ACT ACG GCG AAG TTT GAC TAC
Thr Thr Ala Lys Phe Asp Tyr

SEQ ID NO 13:

CGG GCA AGT CAG AGC ATT AGC AGC TAT TTA AAT
Arg Ala Ser Gln Ser Ile Ser Ser Tyr Leu Asn

SEQ ID NO 14:

TCT GCA TCC CGA TTG CAA AGT
Ser Ala Ser Arg Leu Gln Ser

SEQ ID NO 15:

CAA CAG CTG CAG AGG AAG CCT ACG ACG
Gln Gln Leu Gln Arg Lys Pro Thr Thr

SEQ ID NO 16:

AAPSVFIFPPSDEQLKSGTASVVCLLNNFYPREAKVQWKVDNALQSGNSQESVTEQDSKDST

YSLSSTLTLSKADYEKHKVYACEVTHQGLSSPVTKSFNRGESHHHHHH

SEQ ID NO: 17

ACG GAC ATC CAG ATG ACC CAG TCT CCA TCC TCC CTG TCT GCA
TCT GTA GGA GAC AGA GTC ACC ATC ACT TGC CGG GCA AGT CAG
AGC ATT AGC AGC TAT TTA AAT TGG TAT CAG CAG AAA CCA GGG
AAA GCC CCT AAG CTC CTG ATC TAT TCT GCA TCC CGA TTG CAA
AGT GGG GTC CCA TCA AGG TTC AGT GGC AGT GGA TCT GGG ACA
GAT TTC ACT CTC ACC ATC AGC AGT GTG CAA CCT GAA GAT TTT
GCA ACT TAC TAC TGT CAA CAG CTG CAG AGG AAG CTA CGA CGT
TCG GCC AAG GGA CCA GGT GGA AAT CAA ACG GGC GGC CGC TGC
                                                                                                          notI
ACA

SEQ ID NO: 18

Thr Asp Ile Gln Met Thr Gln Ser Pro Ser Ser Leu Ser Ala
Ser Val Gly Asp Arg Val Thr Ile Thr Cys Arg Ala Ser Gln
Ser Ile Ser Ser Tyr Leu Asn Trp Tyr Gln Gln Lys Pro Gly
Lys Ala Pro Lys Leu Leu Ile Tyr Ser Ala Ser Arg Leu Gln
Ser Gly Val Pro Ser Arg Phe Asn Gly Ser Gly Ser Gly Thr
Asp Phe Thr Leu Thr Ile Ser Ser Val Gln Pro Glu Asp Phe
Ala Thr Tyr Tyr Cys Gln Gln Leu Gln Arg Lys Leu Arg Arg
Ser Ala Lys Gly Pro Gly Gly Asn Gln Thr Gly Gly Arg Cys
Thr

SEQ ID NO: 19

CC ATG GCC GAA GTG CAG CTG TTG GAG TCT GGG GGA GGC TTG GTA
CAG CCT GGG GGG TCC CTG AGA CTC TCC TGT GCA GCC TCT GGA
TTC ACC TTT AGC AGC TAT GCC ATG AGC TGG GTC CGC CAG GCT
CCA GGG AAG GGG CTG GAG TGG GTC TCA ACT ATT GCT GCG TCG
GGT CCT TCT ACA GGG TAC GCA GAC TCC GTG AAG GGC CGG TTC
ACC ATC TCC AGA GAC AAT TCC AAG AAC ACG CTG TAT CTG CAA
ATG AAC AGC CTG AGA GCC GAG GAC ACG GCC GTA TAT TAC TGT
GCG AAA ACT ACG GCG AAG TTT GAC TAC TGG GGC CAG GGA ACC
CTG GTC ACC GTC TCG AGC GGT GGA GGC GGT TCA GGC GGA GGT
                                                                                                         Linker
GGC AGC GGC GGT GGC GGG TCG ACG GAC ATC CAG ATG ACC CAG
TCT CCA TCC TCC CTG TCT GCA TCT GTA GGA GAC AGA GTC ACC
ATC ACT TGC CGG GCA AGT CAG AGC ATT AGC AGC TAT TTA AAT
TGG TAT CAG CAG AAA CCA GGG AAA GCC CCT AAG CTC CTG ATC
TAT TCT GCA TCC CGA TTG CAA AGT GGG GTC CCA TCA AGG TTC AGT GGC AGT GGA TCT GGG ACA GAT TTC ACT CTC ACC ATC AGC
AGT GTG CAA CCT GAA GAT TTT GCA ACT TAC TAC TGT CAA CAG
CTG CAG AGG AAG CTA CGA CGT TCG GCC AAG GGA CCA GGT GGA
                                         notI
AAT CAA ACG GGC GGC CGC TGA ACA TCT GTC TTC ATC TTT ......
                                              Ck - light chain + his tag -continued

SEQ ID NO: 20

```
  1 Met Ala Glu Val Gln Leu Leu Glu Ser Gly Gly Gly Leu Val
 15 Gln Pro Gly Gly Ser Leu Arg Leu Ser Cys Ala Ala Ser Gly
 30 Phe Thr Phe Ser Ser Tyr Ala Met Ser Trp Val Arg Gln Ala
 45 Pro Gly Lys Gly Leu Glu Trp Val Ser Thr Ile Ala Ala Ser
 60 Gly Pro Ser Thr Gly Tyr Ala Asp Ser Val Lys Gly Arg Phe
 75 Thr Ile Ser Arg Asp Asn Ser Lys Asn Thr Leu Tyr Leu Gln
 90 Met Asn Ser Leu Arg Ala Glu Asp Thr Ala Val Tyr Tyr Cys
105 Ala Lys Thr Thr Ala Lys Phe Asp Tyr Trp Gly Gln Gly Thr
120 Leu Val Thr Val Ser Ser Gly Gly Gly Gly Ser Gly Gly Gly
                              Linker
135 Gly Ser Gly Gly Gly Gly Ser Thr Asp Ile Gln Met Thr Gln
150 Ser Pro Ser Ser Leu Ser Ala Ser Val Gly Asp Arg Val Thr
165 Ile Thr Cys Arg Ala Ser Gln Ser Ile Ser Ser Tyr Leu Asn
180 Trp Tyr Gln Gln Lys Pro Gly Lys Ala Pro Lys Leu Leu Ile
195 Tyr Ser Ala Ser Arg Leu Gln Ser Gly Val Pro Ser Arg Phe
210 Ser Gly Ser Gly Ser Gly Thr Asp Phe Thr Leu Thr Ile Ser
225 Ser Val Gln Pro Glu Asp Phe Ala Thr Tyr Tyr Cys Gln Gln
240 Leu Gln Arg Lys Leu Arg Arg Ser Ala Lys Gly Pro Gly Gly
                   notI
255 Asn Gln Thr Gly Gly Arg Cys Thr Ser Val Phe Ile Phe ....
                                    Ck - light chain + his tag
```

The invention claimed is:

1. A antibody or antigen binding portion thereof that binds synaptophysin and said antibody or antigen binding portion thereof comprises the amino acid sequences set forth in SEQ ID NOS:21-26.

2. A antibody or antigen binding portion thereof that binds synaptophysin, comprising a VH domain comprising a CDR1 comprising the amino acid sequence of SEQ ID NO:24, a CDR2 comprising the amino acid sequence of SEQ ID NO:25, and a CDR3 comprising the amino acid sequence of SEQ ID NO:26; said binding member further comprising a VL domain comprising a CDR1 comprising the amino acid sequence of SEQ ID NO:21, a CDR2 comprising the amino acid sequence of SEQ ID NO:22, and a CDR3 comprising the amino acid sequence of SEQ ID NO:23.

3. The antibody or antigen binding portion thereof of claim 2, wherein said antibody or antigen binding portion thereof binds an epitope within the amino acid sequence of SEQ ID NO:9.

4. The antibody or antigen binding portion thereof of claim 2, said antibody or antigen binding portion thereof comprising a VH domain comprising the amino acid sequence of SEQ ID NO:2.

5. The antibody or antigen binding portion thereof of claim 2, said antibody or antigen binding portion thereof comprising a VL domain comprising the amino acid sequence of SEQ ID NO:4.

6. The antibody or antigen binding portion thereof of claim 4, said antibody or antigen binding portion thereof comprising a VL domain comprising the amino acid sequence of SEQ ID NO:4.

7. The antibody or antigen binding portion thereof of claim 6, wherein said antibody or antigen binding portion thereof is selected from a Fab and an scFv.

8. The antibody or antigen binding portion thereof of claim 7, said antibody or antigen binding portion thereof further comprising a linker flanked by said VH and VL domains.

9. The antibody or antigen binding portion thereof of claim 8, wherein said linker comprises the amino acid sequence of SEQ ID NO:6.

10. The antibody or antigen binding portion thereof of claim 9, wherein said antibody or antigen binding portion thereof comprises the amino acid sequence of SEQ ID NO:8.

11. The antibody or antigen binding portion thereof of claim 10, said antibody or antigen binding portion thereof further comprising an antibody constant region.

12. The antibody or antigen binding portion thereof of claim 11, wherein said constant region is a human constant kappa (Cκ) region comprising the amino acid sequence of SEQ ID NO:6.

13. The antibody or antigen binding portion thereof of claim 2, said antibody or antigen binding portion thereof comprising a full-length antibody heavy chain and a full-length antibody light chain.

14. The antibody or antigen binding portion thereof of claim 1 which is conjugated to a detectable label, enzyme, or toxin, optionally directly via a peptidyl bond or via a linker.

15. The antibody or antigen binding portion thereof of claim 14 wherein the toxin is selected from the group comprising tributyl tin and gliotoxin.

16. A antibody or antigen binding portion thereof according to claim 14 wherein the detectable label is FITC.

17. A composition comprising the specific binding member of any one of claims 1-16 and a pharmaceutically acceptable excipient.

* * * * *

SEQUENCE LISTING

<160> NUMBER OF SEQ ID NOS: 27

<210> SEQ ID NO 1
<211> LENGTH: 356
<212> TYPE: DNA
<213> ORGANISM: Homo sapiens

<400> SEQUENCE: 1

```
ccatggccga agtgcagctg ttggagtctg ggggaggctt ggtacagcct ggggggtccc    60
tgagactctc ctgtgcagcc tctggattca cctttagcag ctatgccatg agctgggtcc   120
gccaggctcc agggaagggg ctggagtggg tctcaactat tgctgcgtcg ggtccttcta   180
cagggtacgc agactccgtg aagggccggt tcaccatctc cagagacaat tccaagaaca   240
cgctgtatct gcaaatgaac agcctgagag ccgaggacac ggccgtatat tactgtgcga   300
aaactacggc gaagtttgac tactggggcc agggaaccct ggtcaccgtc tcgagc       356
```

<210> SEQ ID NO 2
<211> LENGTH: 118
<212> TYPE: PRT
<213> ORGANISM: Homo sapiens

<400> SEQUENCE: 2

```
Met Ala Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
        35                  40                  45
```

```
Trp Val Ser Thr Ile Ala Ala Ser Gly Pro Ser Thr Gly Tyr Ala Asp
 50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Ala Lys Thr Thr Ala Lys Phe Asp Tyr Trp Gly Gln Gly Thr
            100                 105                 110

Leu Val Thr Val Ser Ser
        115

<210> SEQ ID NO 3
<211> LENGTH: 339
<212> TYPE: DNA
<213> ORGANISM: Homo sapiens

<400> SEQUENCE: 3
acggacatcc agatgaccca gtctccatcc tccctgtctg catctgtagg agacagagtc      60
accatcactt gccgggcaag tcagagcatt agcagctatt taaattggta tcagcagaaa     120
ccagggaaag cccctaagct cctgatctat tctgcatccc gattgcaaag tggggtccca     180
tcaaggttca atggcagtgg atctgggaca gatttcactc tcaccatcag cagtctgcaa     240
cctgaagatt ttgcaactta ctactgtcaa cagctgcaga ggaagcctac gacgttcggc     300
caagggacca aggtggaaat caaacgggcg gccgctgca                            339

<210> SEQ ID NO 4
<211> LENGTH: 113
<212> TYPE: PRT
<213> ORGANISM: Homo sapiens

<400> SEQUENCE: 4

Thr Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Ser Ile Ser Ser
             20                  25                  30

Tyr Leu Asn Trp Tyr Gln Gln Lys Pro Gly Lys Ala Pro Lys Leu Leu
             35                  40                  45

Ile Tyr Ser Ala Ser Arg Leu Gln Ser Gly Val Pro Ser Arg Phe Asn
 50                  55                  60

Gly Ser Gly Ser Gly Thr Asp Phe Thr Leu Thr Ile Ser Ser Leu Gln
 65                  70                  75                  80

Pro Glu Asp Phe Ala Thr Tyr Tyr Cys Gln Gln Leu Gln Arg Lys Pro
                 85                  90                  95

Thr Thr Phe Gly Gln Gly Thr Lys Val Glu Ile Lys Arg Gly Ala Ala
            100                 105                 110

Ala

<210> SEQ ID NO 5
<211> LENGTH: 45
<212> TYPE: DNA
<213> ORGANISM: Artificial sequence
<220> FEATURE:
<223> OTHER INFORMATION: C1-3 linker encoding nucleotide sequence

<400> SEQUENCE: 5
ggtggaggcg gttcaggcgg aggtggcagc ggcggtggcg ggtcg                      45
```

```
<210> SEQ ID NO 6
<211> LENGTH: 15
<212> TYPE: PRT
<213> ORGANISM: Artificial sequence
<220> FEATURE:
<223> OTHER INFORMATION: C1-3 linker amino acid sequence

<400> SEQUENCE: 6

Gly Gly Gly Gly Ser Gly Gly Gly Gly Ser Gly Gly Gly Gly Ser
1               5                   10                  15

<210> SEQ ID NO 7
<211> LENGTH: 758
<212> TYPE: DNA
<213> ORGANISM: Artificial sequence
<220> FEATURE:
<223> OTHER INFORMATION: C1-3 encoding nucleotide sequence

<400> SEQUENCE: 7
ccatggccga agtgcagctg ttggagtctg ggggaggctt ggtacagcct ggggggtccc      60
tgagactctc ctgtgcagcc tctggattca cctttagcag ctatgccatg agctgggtcc    120
gccaggctcc agggaagggg ctggagtggg tctcaactat tgctgcgtcg ggtccttcta    180
cagggtacgc agactccgtg aagggccggt tcaccatctc cagagacaat tccaagaaca    240
cgctgtatct gcaaatgaac agcctgagag ccgaggacac ggccgtatat tactgtgcga    300
aaactacggc gaagtttgac tactgggggcc agggaaccct ggtcaccgtc tcgagcggtg    360
gaggcggttc aggcggaggt ggcagcggcg gtggcgggtc gacggacatc cagatgaccc    420
agtctccatc ctccctgtct gcatctgtag gagacagagt caccatcact tgccgggcaa    480
gtcagagcat tagcagctat ttaaattggt atcagcagaa accagggaaa gcccctaagc    540
tcctgatcta ttctgcatcc cgattgcaaa gtggggtccc atcaaggttc aatggcagtg    600
gatctgggac agatttcact ctcaccatca gcagtctgca acctgaagat tttgcaactt    660
actactgtca acagctgcag aggaagccta cgacgttcgg ccaagggacc aaggtggaaa    720
tcaaacgggc ggccgctgca ccatctgtct tcatcttt                             758

<210> SEQ ID NO 8
<211> LENGTH: 252
<212> TYPE: PRT
<213> ORGANISM: Artificial sequence
<220> FEATURE:
<223> OTHER INFORMATION: C1-3 amino acid sequence

<400> SEQUENCE: 8

Met Ala Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Thr Phe Ser
                20                  25                  30

Ser Tyr Ala Met Ser Trp Val Arg Gln Ala Pro Gly Lys Gly Leu Glu
            35                  40                  45

Trp Val Ser Thr Ile Ala Ala Ser Gly Pro Ser Thr Gly Tyr Ala Asp
        50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Thr Thr Ala Lys Phe Asp Tyr Trp Gly Gln Gly Thr
            100                 105                 110
```

```
Leu Val Thr Val Ser Ser Gly Gly Gly Gly Ser
        115                 120                 125

Gly Gly Gly Gly Ser Thr Asp Ile Gln Met Thr Gln Ser Pro Ser Ser
        130                 135                 140

Leu Ser Ala Ser Val Gly Asp Arg Val Thr Ile Thr Cys Arg Ala Ser
145                 150                 155                 160

Gln Ser Ile Ser Ser Tyr Leu Asn Trp Tyr Gln Gln Lys Pro Gly Lys
                165                 170                 175

Ala Pro Lys Leu Leu Ile Tyr Ser Ala Ser Arg Leu Gln Ser Gly Val
            180                 185                 190

Pro Ser Arg Phe Asn Gly Ser Gly Ser Gly Thr Asp Phe Thr Leu Thr
        195                 200                 205

Ile Ser Ser Leu Gln Pro Glu Asp Phe Ala Thr Tyr Tyr Cys Gln Gln
    210                 215                 220

Leu Gln Arg Lys Pro Thr Thr Phe Gly Gln Gly Thr Lys Val Glu Ile
225                 230                 235                 240

Lys Arg Gly Ala Ala Ala Pro Ser Val Phe Ile Phe
                245                 250

<210> SEQ ID NO 9
<211> LENGTH: 15
<212> TYPE: PRT
<213> ORGANISM: Homo sapiens

<400> SEQUENCE: 9

Tyr Pro Phe Arg Leu His Gln Val Tyr Phe Asp Ala Pro Ser Cys
1               5                   10                  15

<210> SEQ ID NO 10
<211> LENGTH: 15
<212> TYPE: DNA
<213> ORGANISM: Homo sapiens
<220> FEATURE:
<221> NAME/KEY: CDS
<222> LOCATION: (1)..(15)

<400> SEQUENCE: 10 agc tat gcc atg agc                                                     15
Ser Tyr Ala Met Ser
1               5

<210> SEQ ID NO 11
<211> LENGTH: 51
<212> TYPE: DNA
<213> ORGANISM: Homo sapiens
<220> FEATURE:
<221> NAME/KEY: CDS
<222> LOCATION: (1)..(51)

<400> SEQUENCE: 11 act att gct gcg tcg ggt cct tct aca ggg tac gca gac tcc gtg aag        48
Thr Ile Ala Ala Ser Gly Pro Ser Thr Gly Tyr Ala Asp Ser Val Lys
1               5                   10                  15 ggc                                                                     51
Gly

<210> SEQ ID NO 12
<211> LENGTH: 21
<212> TYPE: DNA
<213> ORGANISM: Homo sapiens
<220> FEATURE:
<221> NAME/KEY: CDS
```

-continued

```
<222> LOCATION: (1)..(21)

<400> SEQUENCE: 12 act acg gcg aag ttt gac tac                                      21
Thr Thr Ala Lys Phe Asp Tyr
1               5

<210> SEQ ID NO 13
<211> LENGTH: 33
<212> TYPE: DNA
<213> ORGANISM: Homo sapiens
<220> FEATURE:
<221> NAME/KEY: CDS
<222> LOCATION: (1)..(33)

<400> SEQUENCE: 13 cgg gca agt cag agc att agc agc tat tta aat                      33
Arg Ala Ser Gln Ser Ile Ser Ser Tyr Leu Asn
1               5                   10

<210> SEQ ID NO 14
<211> LENGTH: 21
<212> TYPE: DNA
<213> ORGANISM: Homo sapiens
<220> FEATURE:
<221> NAME/KEY: CDS
<222> LOCATION: (1)..(21)

<400> SEQUENCE: 14 tct gca tcc cga ttg caa agt                                      21
Ser Ala Ser Arg Leu Gln Ser
1               5

<210> SEQ ID NO 15
<211> LENGTH: 27
<212> TYPE: DNA
<213> ORGANISM: Homo sapiens
<220> FEATURE:
<221> NAME/KEY: CDS
<222> LOCATION: (1)..(27)

<400> SEQUENCE: 15 caa cag ctg cag agg aag cct acg acg                              27
Gln Gln Leu Gln Arg Lys Pro Thr Thr
1               5

<210> SEQ ID NO 16
<211> LENGTH: 110
<212> TYPE: PRT
<213> ORGANISM: Artificial sequence
<220> FEATURE:
<223> OTHER INFORMATION: Entire amino acid sequence for the Human
      constant kappa domain and 6 Histidine residue purification tag

<400> SEQUENCE: 16

Ala Ala Pro Ser Val Phe Ile Phe Pro Pro Ser Asp Glu Gln Leu Lys
1               5                   10                  15

Ser Gly Thr Ala Ser Val Val Cys Leu Leu Asn Asn Phe Tyr Pro Arg
            20                  25                  30

Glu Ala Lys Val Gln Trp Lys Val Asp Asn Ala Leu Gln Ser Gly Asn
        35                  40                  45

Ser Gln Glu Ser Val Thr Glu Gln Asp Ser Lys Asp Ser Thr Tyr Ser
    50                  55                  60

Leu Ser Ser Thr Leu Thr Leu Ser Lys Ala Asp Tyr Glu Lys His Lys
65                  70                  75                  80
```

Val Tyr Ala Cys Glu Val Thr His Gln Gly Leu Ser Ser Pro Val Thr
            85                  90                  95

Lys Ser Phe Asn Arg Gly Glu Ser His His His His His His
            100                 105                 110

<210> SEQ ID NO 17
<211> LENGTH: 339
<212> TYPE: DNA
<213> ORGANISM: Homo sapiens

<400> SEQUENCE: 17
acggacatcc agatgaccca gtctccatcc tccctgtctg catctgtagg agacagagtc      60
accatcactt gccgggcaag tcagagcatt agcagctatt taaattggta tcagcagaaa    120
ccagggaaag cccctaagct cctgatctat tctgcatccc gattgcaaag tggggtccca    180
tcaaggttca gtggcagtgg atctgggaca gatttcactc tcaccatcag cagtgtgcaa    240
cctgaagatt ttgcaactta ctactgtcaa cagctgcaga ggaagctacg acgttcggcc    300
aagggaccag gtggaaatca aacggcggc cgctgcaca                            339

<210> SEQ ID NO 18
<211> LENGTH: 113
<212> TYPE: PRT
<213> ORGANISM: Homo sapiens

<400> SEQUENCE: 18

Thr Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Ile Ser Ser
            20                  25                  30

Tyr Leu Asn Trp Tyr Gln Gln Lys Pro Gly Lys Ala Pro Lys Leu Leu
        35                  40                  45

Ile Tyr Ser Ala Ser Arg Leu Gln Ser Gly Val Pro Ser Arg Phe Ser
    50                  55                  60

Gly Ser Gly Ser Gly Thr Asp Phe Thr Leu Thr Ile Ser Ser Val Gln
65                  70                  75                  80

Pro Glu Asp Phe Ala Thr Tyr Tyr Cys Gln Gln Leu Gln Arg Lys Leu
                85                  90                  95

Arg Arg Ser Ala Lys Gly Pro Gly Gly Asn Gln Thr Gly Gly Arg Cys
            100                 105                 110

Thr

<210> SEQ ID NO 19
<211> LENGTH: 755
<212> TYPE: DNA
<213> ORGANISM: Artificial sequence
<220> FEATURE:
<223> OTHER INFORMATION: An earlier version of the C1-3 encoding
      nucleotide sequence

<400> SEQUENCE: 19
ccatggccga agtgcagctg ttggagtctg ggggaggctt ggtacagcct ggggggtccc      60
tgagactctc ctgtgcagcc tctggattca cctttagcag ctatgccatg agctgggtcc    120
gccaggctcc agggaagggg ctggagtggg tctcaactat tgctgcgtcg gtccttctca    180
cagggtacgc agactccgtg aagggccggt tcaccatctc cagagacaat tccaagaaca    240
cgctgtatct gcaaatgaac agcctgagag ccgaggacac ggccgtatat tactgtgcga    300
aaactacggc gaagtttgac tactggggcc aaggaaccct ggtcaccgtc tcgagcggtg    360

-continued

```
gaggcggttc aggcggaggt ggcagcggcg gtggcgggtc gacggacatc cagatgaccc    420
agtctccatc ctccctgtct gcatctgtag agacagagt caccatcact tgccgggcaa    480
gtcagagcat tagcagctat ttaaattggt atcagcagaa accagggaaa gcccctaagc    540
tcctgatcta ttctgcatcc cgattgcaaa gtggggtccc atcaaggttc agtggcagtg    600
gatctgggac agatttcact ctcaccatca gcagtgtgca acctgaagat tttgcaactt    660
actactgtca acagctgcag aggaagctac gacgttcggc caagggacca ggtggaaatc    720
aaacgggcgg ccgctgcaca tctgtcttca tcttt                              755
```

```
<210> SEQ ID NO 20
<211> LENGTH: 251
<212> TYPE: PRT
<213> ORGANISM: Artificial sequence
<220> FEATURE:
<223> OTHER INFORMATION: An earlier version of the C1-3 amino acid
      sequence

<400> SEQUENCE: 20
```

Met Ala Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
        35                  40                  45

Trp Val Ser Thr Ile Ala Ala Ser Gly Pro Ser Thr Gly Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Thr Thr Ala Lys Phe Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Thr Asp Ile Gln Met Thr Gln Ser Pro Ser Ser
    130                 135                 140

Leu Ser Ala Ser Val Gly Asp Arg Val Thr Ile Thr Cys Arg Ala Ser
145                 150                 155                 160

Gln Ser Ile Ser Ser Tyr Leu Asn Trp Tyr Gln Gln Lys Pro Gly Lys
                165                 170                 175

Ala Pro Lys Leu Leu Ile Tyr Ser Ala Ser Arg Leu Gln Ser Gly Val
            180                 185                 190

Pro Ser Arg Phe Ser Gly Ser Gly Ser Gly Thr Asp Phe Thr Leu Thr
        195                 200                 205

Ile Ser Ser Val Gln Pro Glu Asp Phe Ala Thr Tyr Tyr Cys Gln Gln
    210                 215                 220

Leu Gln Arg Lys Leu Arg Arg Ser Ala Lys Gly Pro Gly Gly Asn Gln
225                 230                 235                 240

Thr Gly Gly Arg Cys Thr Ser Val Phe Ile Phe
                245                 250

```
<210> SEQ ID NO 21
<211> LENGTH: 5
<212> TYPE: PRT
<213> ORGANISM: Homo sapiens
```

```
<400> SEQUENCE: 21

Ser Tyr Ala Met Ser
1               5

<210> SEQ ID NO 22
<211> LENGTH: 17
<212> TYPE: PRT
<213> ORGANISM: Homo sapiens

<400> SEQUENCE: 22

Thr Ile Ala Ala Ser Gly Pro Ser Thr Gly Tyr Ala Asp Ser Val Lys
1               5                   10                  15

Gly

<210> SEQ ID NO 23
<211> LENGTH: 7
<212> TYPE: PRT
<213> ORGANISM: Homo sapiens

<400> SEQUENCE: 23

Thr Thr Ala Lys Phe Asp Tyr
1               5

<210> SEQ ID NO 24
<211> LENGTH: 11
<212> TYPE: PRT
<213> ORGANISM: Homo sapiens

<400> SEQUENCE: 24

Arg Ala Ser Gln Ser Ile Ser Ser Tyr Leu Asn
1               5                   10

<210> SEQ ID NO 25
<211> LENGTH: 7
<212> TYPE: PRT
<213> ORGANISM: Homo sapiens

<400> SEQUENCE: 25

Ser Ala Ser Arg Leu Gln Ser
1               5

<210> SEQ ID NO 26
<211> LENGTH: 9
<212> TYPE: PRT
<213> ORGANISM: Homo sapiens

<400> SEQUENCE: 26

Gln Gln Leu Gln Arg Lys Pro Thr Thr
1               5

<210> SEQ ID NO 27
<211> LENGTH: 14
<212> TYPE: PRT
<213> ORGANISM: Homo sapiens

<400> SEQUENCE: 27

Ala Thr Asp Pro Glu Asn Ile Ile Lys Glu Met Pro Met Cys
1               5                   10
```